United States Patent
Yang et al.

(10) Patent No.: US 12,201,692 B2
(45) Date of Patent: *Jan. 21, 2025

(54) TARGETED PROTEASE COMPOSITIONS AND USES RELATED THERETO

(71) Applicant: Emory University, Atlanta, GA (US)

(72) Inventors: Lily Yang, Atlanta, GA (US); Xiangxue Guo, Lilburn, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,038

(22) Filed: Mar. 22, 2023

(65) Prior Publication Data

US 2023/0416761 A1    Dec. 28, 2023

Related U.S. Application Data

(62) Division of application No. 16/436,055, filed on Jun. 10, 2019, now Pat. No. 11,643,662, which is a division of application No. 15/102,600, filed as application No. PCT/US2014/069106 on Dec. 8, 2014, now Pat. No. 10,335,493.

(60) Provisional application No. 61/913,989, filed on Dec. 10, 2013.

(51) Int. Cl.
| | |
|---|---|
| *A61K 47/64* | (2017.01) |
| *A61K 49/00* | (2006.01) |
| *C12N 9/96* | (2006.01) |
| *C12N 15/63* | (2006.01) |

(52) U.S. Cl.
CPC .......... *A61K 47/64* (2017.08); *A61K 49/0056* (2013.01); *A61K 49/0065* (2013.01); *C12N 9/96* (2013.01); *C12N 15/63* (2013.01); *C12Y 304/00* (2013.01); *C07K 2319/01* (2013.01); *C12N 2810/00* (2013.01)

(58) Field of Classification Search
CPC ..... A61P 35/00; A61K 47/64; A61K 49/0056; A61K 49/0065; C07K 2319/01; C12N 15/63; C12N 2810/00; C12N 9/50; C12N 9/96; C12Y 304/00
See application file for complete search history.

(56) References Cited

U.S. PATENT DOCUMENTS

| | | |
|---|---|---|
| 6,372,205 B1 | 4/2002 | Duncan |
| 8,394,760 B2 | 3/2013 | Yang |
| 8,889,430 B2 | 11/2014 | Yang |
| 9,801,953 B2 | 10/2017 | Yang |
| 10,335,493 B2 | 7/2019 | Yang |
| 11,643,662 B2 | 5/2023 | Yang |
| 2010/0272740 A1 | 10/2010 | Vertegel |
| 2014/0105828 A1 | 4/2014 | Yang |

FOREIGN PATENT DOCUMENTS

| | | | |
|---|---|---|---|
| WO | 2008073856 | 6/2008 | |
| WO | WO-2011156321 A1 * | 12/2011 | ........... A61K 31/341 |
| WO | 2012135562 | 10/2012 | |

OTHER PUBLICATIONS

Abdalla et al. Enhanced noscapine delivery using uPAR-targeted optical-MR imaging trackable nanoparticles for prostate cancer therapy, J Control Release. 2011, 149(3): 314-322.
Buckway et al. Overcoming the stromal barrier for targeted delivery of HPMA copolymers to pancreatic tumors, International Journal of Pharmaceutics 456 (2013) 202-211.
Cho et al. Targeted Delivery of siRNA-Generating DNA Nanocassettes Using Multifunctional Nanoparticles, Small. 2013, 9(11): 1964-1973.
Giannandrea et al. Diverse functions of matrix metalloproteinases during fibrosis, Dis Model Mech. 2014, 7(2): 193-203.
Hansen et al. Targeting of peptide conjugated magnetic nanoparticles to urokinase plasminogen activator receptor (uPAR) expressing cells, Nanoscale, 2013, 5, 8192-8201.
Lee et al. Theranostic Nanoparticles with Controlled Release of Gemcitabine for Targeted Therapy and MRI of Pancreatic Cancer, ACS Nano. 2013, 7(3):2078-89.
Li et al. Delivery of nanomedicines to extracellular and intracellular compartments of a solid tumor, Advanced Drug Delivery Reviews 64 (2012) 29-39.
Liu et al. Expression of MMP-3 and TIMP-3 in gastric cancer tissue and its clinical significance, Oncology Letters 2: 1319-1322, 2011.
Satpathy et al. Active Targeting Using HER-2-Affibody-Conjugated Nanoparticles Enabled Sensitive and Specific Imaging of Orthotopic HER-2 Positive Ovarian Tumors, small 2014, 10, No. 3, 544-555.
Ugwu et al. Proteolytic Cleavage of Urokinase-Type Plasminogen Activator by Stromelysin-1 (MMP-3), Biochemistry 1998, 37, 7231-7236.
Yang et al. Development of Receptor Targeted Magnetic Iron Oxide Nanoparticles for Efficient Drug Delivery and Tumor Imaging, J Biomed Nanotechnol. 2008, 4(4): 439-449.
Yang et al. Receptor-Targeted Nanoparticles for In vivo Imaging of Breast Cancer, Clin Cancer Res. 2009, 15(14): 4722-4732.

(Continued)

*Primary Examiner* — David W Berke-Schlessel
*Assistant Examiner* — Susan E. Fernandez
(74) *Attorney, Agent, or Firm* — Emory Patent Group

(57) ABSTRACT

This disclosure relates to targeted protease compositions and uses related thereto. In certain embodiments, the disclosure relates to nanoparticles wherein a targeting molecule is linked to the nanoparticle and wherein a catalytic domain of a protease is linked to the nanoparticle. In certain embodiments, the targeting molecule and the catalytic domain are within a single polypeptide sequence. In certain embodiments, the targeting molecule binds a molecule more highly expressed on cancer cells then non-cancerous cells, and the nanoparticles disclosed herein are used for the treatment of cancer by further attaching an anti-cancer agent to the nanoparticle or incorporating an anticancer agent within the nanoparticle.

15 Claims, 10 Drawing Sheets

Specification includes a Sequence Listing.

(56) References Cited

OTHER PUBLICATIONS

Yang et al. Molecular Imaging of Pancreatic Cancer in an Animal Model Using Targeted Multifunctional Nanoparticles, Gastroenterology, 2009, 136(5):1514-1525.
Yeole et al., Peptide Nanomedicine in Cancer Treatment, Asian J Pharm Clin Res, vol. 6, Suppl 2, 2013, 28-32.
Zarrabi et al. Inhibition of Matrix Metalloproteinase 14 (MMP-14)-mediated Cancer Cell Migration, The Journal of Biological Chemistry vol. 286, No. 38, pp. 33167-33177, 2011.
Zhang et al. Peptides in cancer nanomedicine: Drug carriers, targeting ligands and protease substrates, Journal of Controlled Release 159 (2012) 2-13.
Zucker et al. Critical appraisal of the use of matrix metalloproteinase inhibitors in cancer treatment, Oncogene. 2000, 19(56):6642-50.

\* cited by examiner

TARGETED PROTEASE COMPOSITIONS AND USES RELATED THERETO

CROSS-REFERENCE TO RELATED APPLICATIONS

This application is a division of U.S. application Ser. No. 16/436,055 filed Jun. 10, 2019, which is a division of U.S. application Ser. No. 15/102,600 filed Jun. 8, 2016 that granted as U.S. Pat. No. 10,335,493 on Jul. 2, 2019, which is the National Stage of International Application No. PCT/US2014/069106 filed Dec. 8, 2014, which claims priority to U.S. Provisional Application No. 61/913,989 filed Dec. 10, 2013. The entirety of each of these applications is hereby incorporated by reference for all purposes.

STATEMENT REGARDING FEDERALLY FUNDED RESEARCH

This invention was made with government support under CA151810 and CA154129A awarded by the National Institutes of Health. The government has certain rights in the invention.

INCORPORATION-BY-REFERENCE OF MATERIAL SUBMITTED AS AN XML FILE VIA THE OFFICE ELECTRONIC FILING SYSTEM

The Sequence Listing associated with this application is provided in XML format and is hereby incorporated by reference into the specification. The name of the XML file containing the Sequence Listing is 13196USDIV2.xml. The XML file is 10 KB, was created on Mar. 21, 2023, and is being submitted electronically via the USPTO patent electronic filing system.

BACKGROUND

Resistance to chemotherapy is a major challenge in treating cancer. The tumor microenvironment includes several barriers to treatment. The tumor stroma promotes proliferation, invasion, metastasis, and chemoresistance. The enriched tumor stromal component and disorganized vasculature of cancer tissues make it extremely difficult to deliver a sufficient amount of therapeutic agents. Thus, there is a need to identify improved therapeutic options.

Tumor targeted delivery can increase bioavailability of a drug to the tumor tissues while reducing systemic toxicity. Urokinase plasminogen activator (uPA) is a serine protease that regulates multiple pathways involved in matrix degradation. Pancreatic cancer tissues have high levels of uPAR expression in tumor cells, tumor endothelial cells, and tumor stromal fibroblasts and macrophages. In contrast, its expression is not found in the normal pancreas or in pancreatic tissues with chronic pancreatitis.

Magnetic iron oxide nanoparticles (IONPs) are a biocompatible and biodegradable nanoparticle. They can be used as molecular imaging probes for targeted magnetic resonance imaging (MRI) and drug delivery. See Yang et al., Receptor-targeted nanoparticles for in vivo imaging of breast cancer, Clin Cancer Res, 2009, 15(14):4722-32. Yang et al., Molecular Imaging of Pancreatic Cancer in an Animal Tumor Model Using Targeted Multifunctional Nanoparticles, Gastroenterology 2009, 136(5): 1514-1525. Lee et al. report engineered urokinase plasminogen activator receptor (uPAR)-targeted magnetic iron oxide nanoparticles (IONPs) carrying chemotherapy drug gemcitabine (Gem) for targeted delivery into uPAR-expressing tumor and stromal cells. ACS Nano, 2013, 7(3):2078-89. See also WO 2008/073856.

Yoele et al., report a review of peptide nanomedicine as it relates to cancer treatment. Asian J Pharma & Clinical, 2013, Supp 2(6), 28. See also Zhang et al., Peptides in cancer nanomedicine: drug carriers, targeting ligands and protease substrates, J Control Release, 2012, 159(1):2-13. Satpathy et al. report active targeting breast cancer cells using HER-2-affibody-conjugated nanoparticles. See Small, 2014, 10(3): 544-55.

Cho et al. report targeted delivery of siRNA-generating DNA nanocassettes using multifunctional nanoparticles. Small, 2013, 9(11):1964-73. See also US Application Publication 2014/0105828.

References cited herein are not an admission of prior art.

SUMMARY

This disclosure relates to targeted protease compositions and uses related thereto. In certain embodiments, the disclosure relates to nanoparticles wherein a targeting molecule is linked to the nanoparticle and wherein a catalytic domain of a protease is linked to the nanoparticle. In certain embodiments, the targeting molecule and the catalytic domain are within a single polypeptide sequence. In certain embodiments, the targeting molecule binds a molecule more highly expressed on cancer cells then non-cancerous cells, and the nanoparticles disclosed herein are used for the treatment of cancer by further attaching an anti-cancer agent to the nanoparticle or incorporating an anticancer agent within the nanoparticle.

In certain embodiments, the disclosure relates to compositions comprising a conjugate comprising a targeting molecule and the catalytic domain of a protease polypeptide and a fluorescent moiety is linked to the protease conjugate or linked to the nanoparticle. Typically, the conjugate is linked to a nanoparticle. In some embodiments, the targeting molecule is linked to the nanoparticle and the protease polypeptide is linked to the nanoparticle. In certain embodiments, a therapeutic agent, e.g., an anti-cancer agent, is linked to the nanoparticle.

In certain embodiments, the targeting molecule is a ligand, folic acid, receptor, tyrosine phosphate inhibitor, steroid, antibody, single chain fragment from the antibody of epidermal growth factor receptor (ScFvEGFR), antibody mimetic, HER-2 affibody, peptide fragment of the receptor binding domain of urokinase plasminogen activator, human insulin like growth factor, or fragment thereof. In certain embodiments, the targeting molecule binds uPAR, EGFR, IGF-1R, or HER-2.

In certain embodiments, the protease is a matrix metalloprotease.

In certain embodiments, particles disclosed herein have two or more targeting molecules and further comprise chemotherapy agents, anti-inflammatory agents, nucleic acids such as siRNAs or nucleic acids such as DNA encoding siRNA in operable combination with a promoter for cellular expression.

In certain embodiments, the disclosure relates to pharmaceutical compositions comprising compositions disclosed herein, and a pharmaceutically acceptable excipient typically for use in the treatment of cancer. In certain embodiments, the pharmaceutical compositions comprise a second anti-cancer agent.

In certain embodiments, the disclosure relates to methods of treating or preventing cancer comprising administering an effective amount of a pharmaceutical composition disclosed herein to a subject in need thereof. In certain embodiments, the pharmaceutical composition is administered in combination with a second anti-cancer agent.

In certain embodiments, the cancer is a stroma-rich cancer such as pancreatic, liver, triple negative breast, prostate, sarcoma, and lung cancer.

In certain embodiments, the compounds are administered or migrate into fibrotic drug resistant residual tumors in cancer patients who have failed previous chemotherapy or Her-2 antibody targeted therapy.

In certain embodiment therapeutic particles disclosed herein are administered to treat or prevent non-cancerous fibrotic tissues with active stroma fibroblasts and macrophages, such as liver cirrhosis, and arteriosclerosis.

In certain embodiments, the disclosure relates to recombinantly produced polypeptides disclosed herein. In certain embodiments, the polypeptide comprises a human uPA sequence or segment thereof configured to bind urokinase plasminogen activator receptor and a catalytic domain of a protease polypeptide. In certain embodiments, the disclosure relates to recombinant nucleic acids encoding the polypeptides disclosed herein. In certain embodiments, the disclosure relates to recombinant vectors comprising recombinant nucleic acids disclosed herein. In certain embodiments, the disclosure relates to expression systems configured to produce recombinant polypeptides disclosed herein comprising vectors disclosed herein.

In certain embodiments, the disclosure relates to targeting uPA-ATF with only the growth factor domain (amino acids 1-68) of ATF having improved solubility and higher uPAR-targeting efficiency. In certain embodiments, the disclosure relates to the fusion targeting ligand ATF68-MMP14 with dual uPAR targeting and MMP14 protease activity.

In certain embodiments, the disclosure relates to $ATF_{MMP}$ conjugated nanoparticles comprising probes and therapeutic drugs wherein the nanoparticles are not limited to magnetic iron oxide nanoparticles.

In certain embodiments, the disclosure relates to targeted nanoparticles conjugated with dual targeting ligands such as $ATF_{MMP}$ and another cancer cell targeted ligand, such as IGF-1, Her2 affibody/antibody, and EGF or single chain antibody against EGFR, to improve targeting and intra-tumoral cell drug delivery in heterogeneous tumor cells.

In certain embodiments, the disclosure relates to nanoparticles disclosed herein comprising near infrared dye, e.g., NIR-830, labeled $ATF_{MMP}$ as peptide targeted optical imaging probes for detection of uPAR receptor expression in tumors, or NIR-830-ATF68-MMP14 conjugated nanoparticle imaging probe for multimodal imaging.

In certain embodiments, the disclosure relates to $ATF_{MMP}$ single or dual targeted nanoparticles carrying chemotherapy drugs, small molecular drugs, siRNAs or siRNA expressing DNA nanocassettes, nucleic acids encoding RNA in operable combination with a promoter.

In certain embodiments, the disclosure contemplates administering an effective amount of nanoparticle disclosed herein in an amount of 0.4 mg to 1.6 mg per kg body weight of the subject. In certain embodiments, dosing treatments of once per week for four to six weeks or more time as necessary are contemplated.

DETAILED DISCUSSION

Figure 1A:
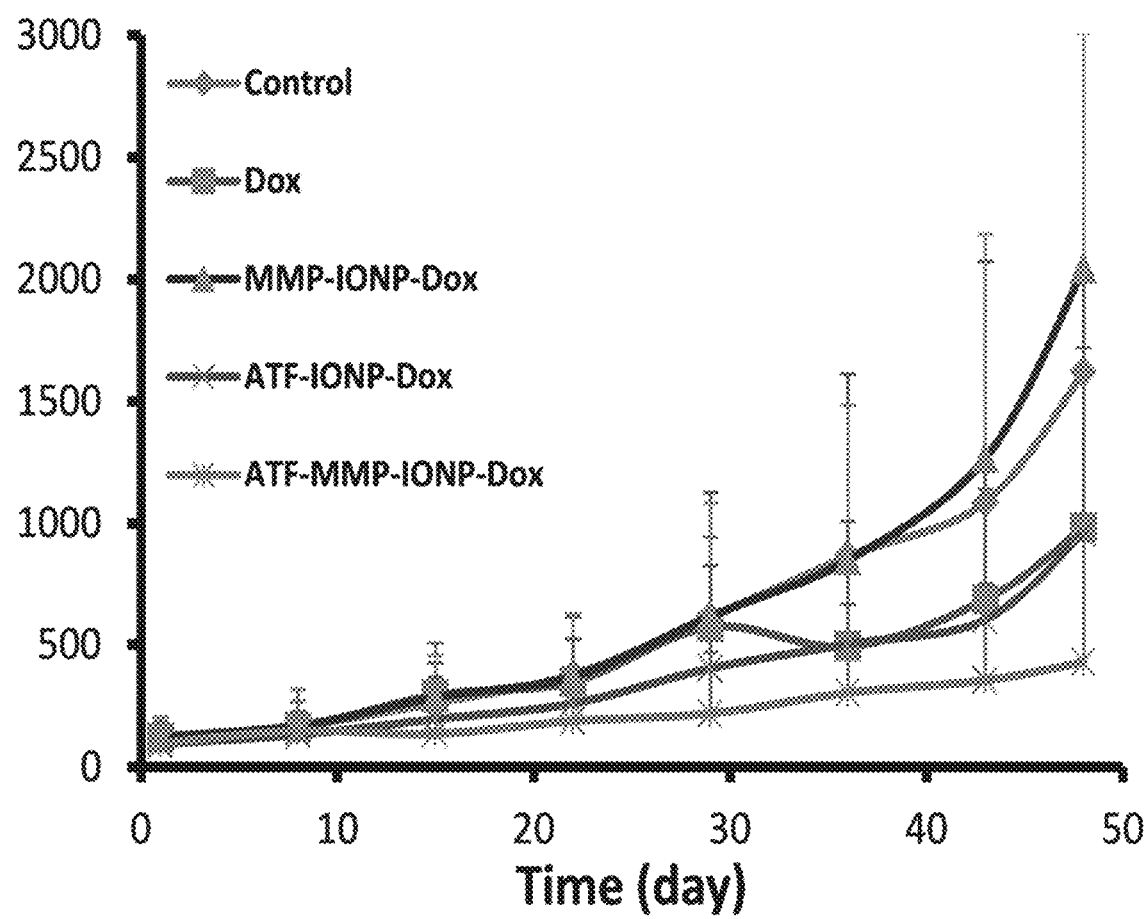
FIG. 1A shows tumor growth curve during the drug treatment by different nanoparticles (NPs). The data indicates MMP protease activity on the targeted nanoparticles enhanced anti-tumor efficiency based on tumor volume.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings unless a contrary intention is apparent.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample particle compared to a control without the particle. It can also be identified by a change in relevant biomarker or gene expression profile, such as PSA for prostate cancer, HER2 for breast cancer, or others.

The terms "nucleic acid sequence" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The terms "a nucleic acid sequence encoding" a specified polypeptide refer to a nucleic acid sequence comprising the coding region of a gene or in other words the nucleic acid sequence which encodes a product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region if needed to permit proper initiation of transcription and/or correct processing of the primary RNA transcript. Alternatively, the coding region utilized in the expression vectors may contain endogenous enhancers, exogenous promoters, splice junctions, intervening sequences, polyadenylation signals, etc., or a combination of both endogenous and exogenous control elements.

The term "recombinant nucleic acid" as used herein is defined as a nucleic acid, e.g., DNA, produced by joining pieces from different sources. The term "recombinant polypeptide" as used herein is defined as a polypeptide produced by using recombinant nucleic acids.

The terms "in operable combination," "in operable order," and "operably linked" refer to the linkage of nucleic acid sequences in such a manner that a nucleic acid molecule capable of directing the transcription of a given gene and/or the synthesis of a desired RNA or protein molecule is produced. Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

The term "expression" when used in reference to a nucleic acid sequence refers to the process of converting genetic information encoded in a gene into RNA (e.g., mRNA, rRNA, tRNA, shRNA, or miRNA) through "transcription" of the gene (i.e., via the enzymatic action of an RNA polymerase), and into protein where applicable (as when a gene encodes a protein), through "translation" of mRNA.

"Expression vector" refers to a vector comprising a recombinant nucleic acid comprising expression control sequences operatively linked to a nucleotide sequence to be expressed. An expression vector comprises sufficient cis-acting elements for expression in an expression system; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant nucleic acid.

Methods of introducing and expressing genes and producing and isolating polypeptides associated with the genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a nucleic acid into a host cell include calcium phosphate precipitation, lipofection, particle bombardment, microinjection, electroporation, and the like.

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape.

Regardless of the method used to introduce exogenous nucleic acids into a host cell or otherwise expose a cell to the nucleic acid, in order to confirm the presence of the recombinant DNA sequence in the host cell, a variety of assays may be performed. Such assays include, for example, "molecular biological" assays well known to those of skill in the art, such as Southern and Northern blotting, reverse transcription polymerase chain reaction (RT-PCR) and PCR; "biochemical" assays, such as detecting the presence or absence of a particular peptide, e.g., by immunological means (ELISAs and Western blots).

Cell-free translation systems are commercially available and many different types and systems are well-known. Examples of cell-free systems include prokaryotic lysates such as *Escherichia coli* lysates, and eukaryotic lysates such as wheat germ extracts, insect cell lysates, rabbit reticulocyte lysates, frog oocyte lysates and human cell lysates. Eukaryotic extracts or lysates may be preferred when the resulting protein is glycosylated, phosphorylated or otherwise modified. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3, elongation factor T (EF-Tu), or termination factors.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include non-natural peptides, recombinant peptides, synthetic peptides, or a combination thereof.

Sequence "identity" refers to the number of matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example, the polypeptides GGGGGG (SEQ ID NO: 7) and GGGGT (SEQ ID NO: 8) have a sequence identity of 4 out of 5 or 80%. For example, the polypeptides GGGPPP (SEQ ID NO: 9) and GGGAPPP (SEQ ID NO: 10) have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted, or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

As used herein, the term "derivative" refers to a structurally similar compound that retains sufficient functional attributes of the identified compound. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxyl group, replacing an aromatic CH with a nitrogen or sulfur. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, alkanoyl, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkanoyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

The term "optionally substituted," as used herein, means that substitution is optional and therefore it is possible for the designated atom to be unsubstituted.

The term "nanoparticle" refers to a molecular conglomerate of about between 1 and 1000 nm in diameter. One more molecules or biomolecules linked to the nanoparticle typically refers to covalently attaching the molecules or biomolecules to a polymer based exterior or coating. Within certain embodiment, the compositions and methods disclosed herein may be utilized with a variety of polymer coated particle such as, e.g., quantum dots (QDs), metal particles, gold, silver, iron, and iron-oxide nanoparticles (IONPs).

IONPs are typically prepared with a mean particle diameter of 4-100 nm. IONPs may be prepared by aging a stoichiometric mixture of ferrous and ferric salts in aqueous media under basic conditions. Control over particle size (2-20 nm) and shape is provided by adjusting the pH, ionic strength and the concentration of the growth solution. The nanoparticles can be functionalized in situ using additives such as organic compounds (e.g. sodium citric) or polymers (e.g. dextran, polyvinyl alcohol). Other metals such as gold, cobalt, nickel, and manganese may be incorporated into the material.

High-temperature decomposition of $Fe(CO)_5$ in organic solvents is another way to prepare IONPs. Size (3-19 nm) can be varied using alternative temperatures. Flame spray pyrolysis yields a range of magnetite, maghemite and wustite (FeO) particles IONPs. Iron precursor such as $Fe(CO)_5$ and $Fe(NO_3)_3$ may be used. Flame spray pyrolysis can be used to produce different nanoparticles ($TiO_2$, $ZrO_2$, silica, etc.) as well as hybrid particles (e.g. silica-IONPs).

Hydroxyl groups on the IONP provide a place for synthetic attachment of different functional groups. A range of chemistries can be used to stabilize metal nanoparticles, exploiting electrostatic, hydrophobic, chelating, and covalent interactions. Carboxylic acid groups can interact with the surface of IONPs by coordination processes. IONP synthesis in organic solvents is typically conducted in oleic acid. A polymer coating on the IONPs is preferred. Polymer attachment to the IONP surface by an initiator fixed to the surface of the IONPs and the polymer is grown from the surface. Alternatively, a functional, pre-formed polymer is grafted onto IONPs in situ. Copolymers with hydrophobic groups, carboxylic acid groups, polyethylene glycols, or amine groups are contemplated. Polymers with a hydrophilic block and a hydrophobic block are contemplated. See Yang et al., Clin Cancer Res, 2009 15:4722; Lin et al., Small, 2008, 4(3):334-341; Yu et a., Nanotechnology, 2006, 17:4483-4487; Park et al., J. Mater. Chem., 2009, 19, 6412-6417; Boyer et al. NPG Asia Mater., 2010, 2(1):23-30, Kim et al., Nanotechnology, 2011, 22, 155101; all hereby incorporated by reference in their entirety.

Linking molecules or polypeptides to the polymers can be accomplished using a variety of methods. Typically, primary amine containing compounds and proteins may be conjugated to the carboxylic acid groups on the polymer mediated by a coupling reagent such as EDAC. See Yang et al., Small, 2009, 5(2):235-43, hereby incorporated by reference in its entirety. Other coupling methods are contemplated, e.g., poly-histidine sequence may be recombinantly incorporated into a polypeptide sequence of the targeting molecule. A poly-histidine chelating agent may be coupled to the polymer surface, e.g., NTA-Ni. Mixing the histidine tagged polypeptide sequence attaches it to the polymer surface linked through the chelating agent. The avidin/streptavidin-biotin interactions may be used, e.g., biotin may be coupled to the polymer surface and streptavidin may be expressed as a fusion/chimera with the targeting molecule.

Targeted Protease Compositions and Conjugated Nanoparticles

One of the major challenges in cancer treatment is that the majority of drug and drug candidates are impeded by the high-density stromal matrix that surrounds cancer cells. It can take several days for an antibody therapeutic to get into the tumor center. The major obstacle are: 1) abnormal vasculatures in tumors, both low vessel density in hypoxic tumor region and immature, non-function blood vessels in tumor areas with active angiogenesis; 2) high interstitial pressure in the tumor due to inflammation and dysfunction in lymphatic drainage system; and 3) extensive tumor stroma and fibrosis in the tumor, e.g., over 50% of pancreatic tumor mass is tumor stroma.

Although it is not intended that embodiments of the disclosure are limited by any particular mechanism, it is believed that nanoparticles targeted to tumor endothelial cells, tumor associated stromal fibroblast and macrophages will facilitate the nanoparticles navigating though the tumor endothelial cell layer and entering into tumor stroma. Interactions of the nanoparticles with tumor stromal cells allows the nanoparticles retaining in the stroma for extended periods of time and the MMP-14$_{CD}$ on the targeting ligand breaking downs the extracellular matrix, which enable immigration of the nanoparticles in the tumor stroma to reach to cancer cells. Therefore, it is desirable to use targeting nanoparticles containing MMP14$_{CD}$ to overcome the tumor stromal barrier and improve efficiency of drug delivery into tumor cells.

Disclosed herein are nanoparticles linked with a protease MMP14$_{CD}$, i.e., the catalytic domain of a broad extracellular matrix metallopeptidase MT1-MMP. Experiments indicate that it functions to localized degradation of components of extracellular matrix (ECM) and shows substrate specificity on the stromal matrix by degrading stromal matrix and breaking the physical barrier of drug delivery. Such an approach has potential to increase drug delivery in many types of human cancer. It is contemplated to be particularly useful for the treatment of pancreatic cancer and triple negative breast cancer since 30 to 50% of those human cancer tissues consist of tumor stoma. It is believed they have the ability to migrate inside the tumor tissue improving drug delivery into tumor cells and overcoming drug resistance by delivering large amounts of anti-cancer agents into tumor cells.

In one example, magnetic iron oxide nanoparticles (IONPs) were used that are targeted to urokinase plasminogen activator receptor (uPAR), which is a cell surface receptor that is highly expressed in tumor endothelial, stromal fibroblasts and active macrophages, and cancer cells. Methods for carrying various therapeutic agents in or on the IONPs are contemplated. Targeted optical and MR imaging, as well as targeted therapeutic effect in breast and pancreatic cancer animal models are contemplated.

In certain embodiments, the disclosure relates to compositions comprising conjugates comprising a targeting molecule and a protease polypeptide. Typically, the conjugate is linked to a nanoparticle. In certain embodiments, the targeting molecule is linked to the nanoparticle and the protease polypeptide is linked to the nanoparticle.

In certain embodiments the disclosure relates to a nanoparticle comprising a recombinant fusion polypeptide comprising a human uPA sequence or segment thereof configured to bind urokinase plasminogen activator receptor (uPAR) and a human metalloprotease sequence or segment thereof configured to catalyze the degradation of an extracellular matrix protein such as, but not limited to, MMPP14, MMP15, MMPP16, and MMPP17, metalloelastase (MMPP12), collegenases (MMP1, MMP8, MMP13), gelatinases (MMP2, MMP9), stromelysins (MMP3, MMP10, MMP11), matrilysin (MMP7, MMP26), enamelysin (MMP20). Typically, the catalytic domain forming the active site comprises a zinc-binding motif of three histidine residues found in the conserved sequence HEXXHXXGXXH (SEQ ID NO: 5) wherein X is individually at each occurrence any amino acid.

In certain embodiments, the disclosure relates to recombinantly produced polypeptides comprising a human uPA sequence or segment thereof configured to bind urokinase plasminogen activator receptor which comprises SEQ ID NO: 2 or a polypeptide with greater than 30% sequence identity or similarity thereto and a catalytic domain of a protease polypeptide which comprises SEQ ID NO: 3 or a polypeptide with greater than 30% sequence identity or similarity thereto.

In certain embodiments, the disclosure relates to recombinant polypeptides comprising or consisting of SEQ ID NO: 4, variants, or sequences with greater than 30%, 40%, 50%, 60%, 70%, 80%, 90%, or 95% sequence identity or similarity thereto.

In certain embodiments, the disclosure relates to recombinant polypeptides comprising or consisting of a human uPA fragment sequence of less than 135, 100, 90, 80, 70, 60, 50, 40, 30 amino acids, e.g., SEQ ID NO:2, variants, or sequences with greater than 30%, 40%, 50%, 60%, 70%, 80%, 90%, or 95% sequence identity or similarity thereto and a catalytic domain of a human matrix metalloprotease, e.g., SEQ ID NO: 3, variants, or sequences with greater than 30%, 40%, 50%, 60%, 70%, 80%, 90%, or 95% sequence identity or similarity thereto.

In certain embodiments, the fusion polypeptides disclosed herein may contain one or more linking groups or amino acid spacers between the targeting sequence and the protease sequence.

In certain embodiments, the core of the nanoparticle has a hydrodynamic size of about between 10 nm to 100 nm, or 10 nm to 40 nm, or 20 nm to 200 nm, or 5 nm to 500 nm in diameter. In certain embodiments, the nanoparticle comprises a core with an average size of about between 2 and 200 nm, or 5 and 100 nm, or 10 and 50 nm. In certain embodiments, the core comprises iron, gold, silver, selenium, zinc, indium, copper, oxygen, sulfur, phosphorus, or combinations thereof. In certain embodiments, the core is a metal, combination of metals, a semiconductor, quantum dot, gold, silver, iron, or an iron oxide particle. A 10 nm core size and hydrodynamic size of 20 to 30 nm were used in certain embodiments.

In certain embodiments, the targeting molecule is a polypeptide ligand, growth factors, protein, antibody, or antibody fragment. In certain embodiments, the cell targeting molecule is a ligand that targets a receptor specifically expressed on tumor cells. In certain embodiments, the cell targeting molecule is human or mouse ATF (hATF or mATF) peptide or fragment thereof. In certain embodiments, the cell targeting molecule is a tumor-targeting human monoclonal antibody or comprises a single-chain variable fragment (scFv) thereof.

In certain embodiments, particles disclosed herein further comprising an anticancer agent.

In certain embodiments, the anticancer agent is conjugated to the polymer coating through carboxylic acid groups. In certain embodiments, the anticancer agent is contained inside the polymer coating in the area of hydrophobic groups.

In certain embodiments, a therapeutic agent is linked to or encapsulated in the nanoparticle. In certain embodiments, therapeutic agent is an anticancer agent such as, but not limited to, temozolamide, gefitinib, erlotinib, docetaxel, cisplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, lenalidomide, or combinations thereof.

In certain embodiments, nanoparticles and protease conjugates disclosed herein comprise a lysosomally degradable molecule linked to a therapeutic agent, e.g., wherein degradable molecule is the polypeptide GFLG (SEQ ID NO: 1) linked to the therapeutic agent. See Lee et al. report engineered urokinase plasminogen activator receptor (uPAR)-targeted magnetic iron oxide nanoparticles (IONPs) carrying chemotherapy drug gemcitabine (Gem) for targeted delivery into uPAR-expressing tumor and stromal cells. See ACS Nano, 2013, 7(3):2078-89.

In certain embodiments, a near infrared dye can be conjugated to the protease-linked targeting ligands and nanoparticles, providing optical imaging capability. In certain embodiments, the dye is a (3,3-dimethyl-indol-1-ium-1-yl)-N-alkylsulfonate dye or salt thereof such as one of the formula:

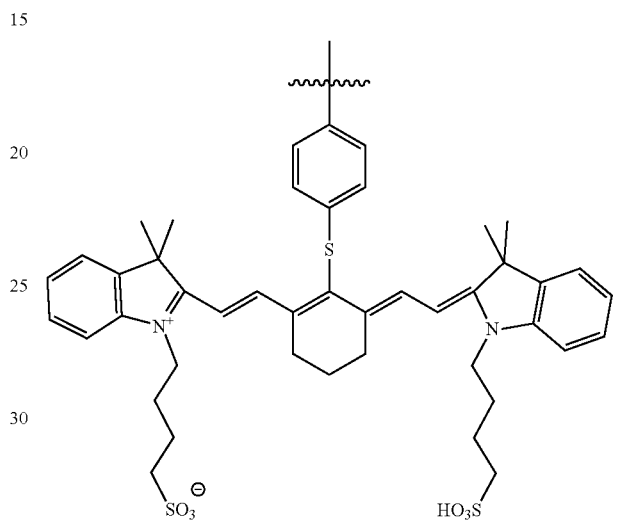

or salts or derivatives thereof optionally substituted with one or more substituents.

In certain embodiments, a fluorescent moiety is linked to the protease conjugate or linked to the nanoparticle. In certain embodiments, the fluorescent moiety is a fluorescent dye, for example, NIR-830 dye, or a fluorescent protein, for example, green fluorescent protein.

In certain embodiments, the targeting molecule binds uPAR, EGFR, or HER-2, PMSA, IGF-1R, folate receptor, transferrin receptor, MUC-1, integrin alphav beta3, cell surface nucleolin, CTLA-4, or VEGFR. In certain embodiments, the targeting molecule is an antibody or antibody mimetic, or aptamer of a natural ligand thereof such as the amino-terminal fragment of uPA, EGF, or folic acid.

In certain embodiments, the disclosure relates to targeting molecule-protease or ligand-protease fusion peptides, recombinant nucleic acids encoding the fusions polypeptides, recombinant vectors comprising the nucleic acids, and expression systems producing the polypeptides.

Methods of Use

In certain embodiments, the ligand-protease fusion peptide is conjugated to nanoparticles for use as an efficient drug delivery system by breaking the tumor stromal barrier. In one example, a receptor targeting ligands was fused with a catalytic domain of a protease to produce a recombinant multifunctional targeting ligand with the ability of targeting to cell surface receptor and digest extracellular matrix in the tumor stroma. Examples of targeting ligands that bind to cell surface receptors highly expressed in tumor cells or tissues include, but are not limited to, amino terminal fragments (ATF) of urokinase plasminogen activator (uPA), IGF-1, EGF, Her-2 affibody, or other tumor homing short peptides.

Examples of proteases include but are not limited to MMP-14, MMP1, MMP9, hyalurondase.

For example, the cDNA sequence of 68 amino acids of the receptor binding domain of uPA was fused with the catalytic domain of the MMP14. Recombinant targeting ligands with uPAR targeting ability and MMP14 activity (ATF68-MMP14$_{CD}$) was produced. ATF68-MMP14$_{CD}$ peptides were conjugated to surface functionalized magnetic iron oxide nanoparticles (IONPs) or quantum dots. Target specificity and enhanced delivery of the nanoparticles have been demonstrated in vivo in animal tumor models. The ATF68-MMP14$_{CD}$ peptides can be used to target nanoparticles carrying therapeutic agents, such as doxorubicin, gemcitabine, and cisplatin. Although it is not intended that embodiments of this disclosure be limited by any particular mechanism, these protease-linked IONPs are believed to have the ability to break tumor stromal matrix and migrate inside tumor tissue to improve intratumoral nanoparticle distribution and potentially increase drug delivery into tumor cells.

The protease conjugates and targeted nanoparticles have broad applications in targeted cancer therapy for many types of human cancers that have extensive tumor stromal components, such as pancreatic, triple negative breast, skin, head and neck, liver, sarcoma, lung, and prostate cancers.

In certain embodiments, the disclosure relates to methods of treating or preventing cancer comprising administering an effective amount of a pharmaceutical composition disclosed herein to a subject in need thereof. In certain embodiments, the pharmaceutical composition is administered in combination with a second anti-cancer agent. In certain embodiments, the cancer is selected from Hodgkin and non-Hodgkin lymphoma, leukemia, cervical cancer, ovarian cancer, endometrial cancer, colon cancer, breast cancer, gastric cancer, lung cancer, renal cancer, ovarian cancer, pancreatic cancer, prostate cancer, glioblastoma, head cancer, neck cancer, thyroid cancer, and melanoma and non-melanoma skin cancer.

In certain embodiments, the disclosure relates to methods of optical and MR imaging the nanoparticle in tumors. 3D-MRI enables monitoring of intratumoral distribution of nanoparticles and tumor responses to therapeutics contained on or in the nanoparticles.

In certain embodiments, the disclosure relates to nanoparticles coated with amphiphilic polymers conjugated with molecules useful for targeting tumors, monitoring the location of the nanoparticles administered to a subject by MRI, and viewing the presence of the nanoparticles during optical image-guided surgery.

In certain embodiments, the disclosure relates to uses of particles disclosed herein as a theranostics. Theranostics are therapeutics with physical properties that allows one to image molecular accumulation of the vehicles in vivo. Yang et al., WO/2007/018647, disclose binding and internalization of tumor targeted-iron oxide particles using MRI. See also Yang et al., J. Biomed. Nanotechnol., 2008, 4, 439-449. Lammers et al., Biomaterials, 2009, 30(2):3466-3475, disclose the simultaneous delivery of doxorubicin and gemcitabine to tumors in vivo using polymeric drug carriers.

In certain embodiments, the disclosure relates to methods comprising preoperatively administering a composition comprising nanoparticles disclosed herein and monitoring the location of the particles in the subject by detecting it by MRI (magnetic resonance imaging) in an area of the subject. In certain embodiments, the method further comprises the steps of operating on the subject in the area of detected particles, imaging dye identified tumors binding the targeting molecule, and surgically removing dye identified tumors or tissue.

In certain embodiments, the disclosure relates to methods comprising preoperatively administering cancer targeted nanoparticles conjugated to dyes disclosed herein to a subject, optically imaging a tumor that bind the nanoparticles intra-opertively, and removing tumors targeted with the nanoparticles.

In certain embodiments, the disclosure contemplates imaging and effecting cell lysis with nanoparticles using iron or iron oxide cores. See WO 2009/120702. In certain embodiments, the disclosure relates to targeting of cancer by local hyperthermia using composition and methods disclosed herein. Local hyperthermia can lead to induction of apoptosis, heat-shock protein release, and chemotherapy agent sensitivity of cancer cells by exposure of cancer cells containing particles with an iron or iron oxide core to an alternating magnetic fields (<1000 kHz) that are safe to normal cells.

In certain embodiments, the disclosure relates to methods for lysis of a cancer cells comprising, administering to a subject nanoparticles disclosed herein and adjusting magnetic fields proximate the subject to cause cell lysis of cancer cell that absorb the particles after administration. Typically, the magnetic field is an oscillating magnetic field and the particles are heated to at least 37° C. in vivo typically greater than 41° C.

In certain embodiments, the disclosure relates to ATF$_{MMP}$ single or dual targeted nanoparticles carrying chemotherapy drugs, small molecular drugs, siRNAs or siRNA expressing DNA nanocassettes, nucleic acids encoding RNA in operable combination with a promotor such as U6. See US Application Publication 2014/0105828.

In certain embodiments, the nucleic acid is double stranded DNA having between about 350 and 1500 base pairs or 400 and 1000 base pairs, or 550 and 750 base pairs. In certain embodiments, the polymer coating contains monomers with hydrophobic and hydrophilic groups.

In certain embodiments, the hydrophilic groups are amine and carboxylic acid groups. In certain embodiments, the nucleic acid is double stranded DNA. In certain embodiments, the RNA capable of RNA interference is RNA that forms a hairpin. In certain embodiments, the RNA capable of RNA interference is a short hairpin RNA. In certain embodiments, the RNA capable of RNA interference comprises a survivin sequence of greater than 15, 16, 17, or 18 nucleotides. In certain embodiments, the promoter is U6 or H1. Human survivin mRNA sequence (also known as *Homo sapiens* baculoviral IAP repeat containing 5 (BIRC5) transcript variant 1) is ACCESSION NM_001168.2, hereby incorporated by reference. An example siRNA sense survivin sequence is:

```
                                            (SEQ ID NO: 6)
       5'-GAGGCTGGCTTCATCCACTGCCC-3';
```

In certain embodiments, the polymer coating is conjugated to a nucleic acid that encodes microRNA.

In certain embodiments, the core of the particle has a size of about between 5 nm and 100 nm, or 20 nm and 200 nm, or 5 nm and 500 nm in diameter. In certain embodiments, the core is a metal, combination of metals, a semiconductor, quantum dot, gold, silver, iron, or an iron oxide particle.

In certain embodiments, the cell targeting molecule is a polypeptide, ligand, receptor, protein, antibody, or antibody fragment. In certain embodiments, the cell targeting molecule is a ligand that targets a receptor specifically expressed on tumor cells. In certain embodiments, the cell targeting molecule is human ATF (hATF) peptide or fragment thereof. In certain embodiments, the cell targeting molecule is a tumor-targeting human monoclonal antibody or comprises a single-chain variable fragment (scFv) thereof.

In certain embodiments, particles disclosed herein further comprising an anticancer agent.

In certain embodiments, the anticancer agent is conjugated to the polymer coating through carboxylic acid groups. In certain embodiments, the anticancer agent is trapped inside the polymer coating in the area of the hydrophobic groups.

In certain embodiments, the disclosure relates to methods of treating a disease or condition associated with an overexpression of a gene comprising administering particles disclosed herein with a polymer coating wherein the polymer is conjugated to a nucleic acid that encodes a RNA capable of RNA interference of the overexpressed gene in operable combination with a promoter and wherein the polymer is conjugated to a cell targeting molecule to a subject in need thereof in an effective amount.

In certain embodiments, the disease or condition is cancer and the subject is diagnosed with cancer. In certain embodiments, the cancer is breast or pancreatic cancer. In certain embodiments, the particles are administered in combination with another anticancer agent.

Targeting Molecules

In certain embodiments, the targeting molecule binds a molecule more highly expressed on cancer cells then non-cancerous cells. Protease conjugates and nanoparticles disclosed herein can be used for the treatment of cancer by further attaching an anti-cancer agent, e.g., to the protease conjugate or nanoparticle or incorporating an anticancer agent within the nanoparticle.

In certain embodiments, the targeting molecule is a ligand, growth factor IGF-1, folate, receptor, inhibitor, steroid, antibody, single chain fragment from the antibody of epidermal growth factor receptor (ScFvEGFR), antibody mimetic, HER-2 affibody, ATF of uPA, or fragment thereof. In certain embodiments, the targeting molecule binds uPAR, EGFR, IGF-1R, or HER-2.

Urokinase plasminogen activator (uPA) is a serine protease that regulates multiple pathways involved in matrix degradation, cell motility, metastasis and angiogenesis. Interaction of the N-terminal growth factor domain of uPA with its cellular receptor (uPAR) results in the conversion of the plasminogen to a serine protease. In addition to its role in activation of the process for degradation of extracellular matrix, uPAR also activates α5β1 integrin and ERK signaling through interaction with EGFR and induces cell proliferation. Additionally, the uPA/uPAR complex can bind to the matrix protein, vitronectin, in association with transmembrane integrins, and activate intracellular signaling molecules such as the protein kinases, promoting cell adhesion, proliferation, and migration.

The cellular receptors for uPA (uPAR) are highly expressed in many human tumor cells, intratumoral fibroblasts and tumor endothelial cells. About 54% of ductal carcinoma in situ (DCIS) and 73% of lobular carcinoma tissues have over 50% of their cancer cells overexpressing uPAR. An elevated level of uPAR is associated with tumor aggressiveness, the presence of distant metastasis and poor prognosis. However, uPAR is undetectable in the majority of normal tissues or organs except for low levels expressed in macrophages, granulocytes, the uterus, thymus, kidney and spleen. Therefore, uPAR is an excellent molecular target for recruiting nanoparticles to breast tumor sites.

The uPAR-binding domain of uPA is located to the amino-terminal fragment (ATF) of uPA. Studies have shown that ATF is a potent uPA binding antagonist to its high affinity receptor (uPAR) at the surface of both tumor and endothelial cells. Systemic or local delivery of a non-catalytic amino-terminal fragment (ATF) of uPA (residues 1-135) using an adenoviral vector or conjugated peptides prevents the formation of the uPA/uPAR complex, thus inhibiting tumor growth and angiogenesis. Yang et al., Clin Cancer Res., 2009, 15(14):4722-32, discuss the preparation of targeted iron oxide nanoparticle using a recombinant peptide containing the amino-terminal fragment of urokinase-type plasminogen activator (uPA) conjugated to magnetic iron oxide nanoparticles amino-terminal fragment conjugated-iron oxide nanoparticle (ATF-IONP). This nanoparticle targets uPA receptor, which is overexpressed in breast cancer tissues.

The human epidermal growth factor receptor (EGFR) family includes EGFR (HER-1), EGFR-2 (HER-2), EGFR-3 (Her-3) and EGFR 4 (HER-4). The ligands that bind to EGFRs are divided into EGFR-like ligands such as EGF and TGF-α, and the heregulins. These ligands bind to EGFR monomers to promoter receptor dimerization and oligomerization that ultimately results in the activation of the EGFR signaling pathway. This EGFR signaling pathway plays a role in the regulation of cell proliferation, survival and differentiation.

Human breast carcinomas express high levels of the EGF receptors. Overexpression of this receptor has been associated with highly aggressive breast cancer types and a poor response to therapeutic agents. Prior preclinical and clinical studies have shown that blocking the EGFR via monoclonal antibodies or inhibition of EGFR tyrosine kinase with small molecule inhibitors inhibits the growth of breast cancers and sensitize chemotherapy responses. Single-chain antibodies to EGFR that contain the specific EGFR binding region but lack the Fc region have been isolated from human scFv phage display libraries. Yang et al., Small, 2009, 5(2):235-43, hereby incorporated by reference in its entirety, discussed the preparation of EGFR targeted nanoparticles conjugating a single-chain anti-EGFR antibody (ScFvEGFR).

Iron oxide nanoparticles conjugated to a purified antibody that selectively binds to the epidermal growth factor receptor (EGFR) deletion mutant (EGFRvIII) present on human glioblastoma multiforme (GBM) cells were used for therapeutic targeting and MRI contrast enhancement of experimental glioblastoma, both in vitro and in vivo, after convection-enhanced delivery (CED). See Hadjipanayis et al., Cancer Res, 2010, 70:6303, hereby incorporated by reference in its entirety. In certain embodiments, the disclosure relates to targeting molecule that is an antibody or antibody mimetic to EGFR or EGFRvIII for use in treating glioblastoma multiforme.

In certain embodiments, the targeting molecule is a monoclonal antibody-610 that targets a surface antigen for use in treating colon carcinoma. See Cerdan et al., Magn Reson Med, 1989, 12:151-63 1989, hereby incorporated by reference in its entirety.

In certain embodiments, the targeting molecule is an antibody to carcinoembryonic antigen (CEA) that targets CEA for use in treating colon tumors. See Tiefenauer et al., Magn Reson Imaging, 1996, 14:391-402, hereby incorporated by reference in its entirety.

In certain embodiments, the targeting molecule is a monoclonal antibody L6 that targets a surface antigen for use in treating intracranial tumor. See Remsen et al., Am J Neuroradiol, 1996, 17:411-18, hereby incorporated by reference in its entirety.

In certain embodiments, the targeting molecule is transferrin that targets transferrin receptor for use in treating carcinoma. See Kresse et al., Magn Reson Med, 1998, 40:236-42, hereby incorporated by reference in its entirety.

In certain embodiments, the targeting molecule is a monoclonal antibody to Her-2, e.g., Herceptin, that targets Her-2 receptors for use in treating breast cancer. See Lee et al., Nat Med, 2007, 13:95-9; Artemov et al., Magn Reson Med, 2003, 49:403-8; and Huh et al., J Am Chem Soc, 2005, 127:12387-91, all hereby incorporated by reference in their entirety.

In certain embodiments, the targeting molecule is the EPPT peptide that targets underglycosylated mucin-1 antigen (uMUC-1) for use in treating breast, colon, pancreas and lung cancer. See Moore et al., Cancer Res, 2004, 64:1821-7, hereby incorporated by reference in its entirety.

In certain embodiments, the targeting molecule is folic acid that targets folate receptor for use in treating mouth carcinoma and cervical cancer, e.g., folic acid as co-targeting ligand with ATF-MMP14. See Chen et al., PDA J Pharm Sci Technol, 2007, 61:303-13; Sun et al., Small, 2006, 4:372-9; and Sonvico et al., Bioconjug Chem, 2005, 16:1181-8, all hereby incorporated by reference in their entirety.

In certain embodiments, the targeting molecule is methotrexate that targets folate receptor for use in treating cervical cancer. See Kohler et al., Langmuir, 2005, 21:8858-64, hereby incorporated by reference in its entirety.

In certain embodiments, the targeting molecule is a monoclonal antibody A7 that targets colorectal tumor antigen for use in treating colorectal carcinoma. See Toma et al., Br J Cancer, 2005, 93:131-6, hereby incorporated by reference in its entirety.

In certain embodiments, the targeting molecule is chlorotoxin peptide that targets membrane-bound matrixmetalloproteinase-2 (MMP-2) for use in treating glioma. See Veiseh et al., Nano Lett, 2005, 5:1003-8, hereby incorporated by reference in its entirety.

In certain embodiments, the targeting molecule is F3 peptide that targets surface-localized tumor vasculature for use in treating glioma. See Reddy et al., Clin Cancer Res, 2006, 12:6677-86, hereby incorporated by reference in its entirety.

In certain embodiments, the targeting molecule is RGD or RGD4C that targets integrins for use in treating melanoma and epidermoid carcinoma. See Zhang et al., Cancer Res, 2007, 67:1555-62 and Uchida et al., J Am Chem Soc, 2006, 128:16626-33, both hereby incorporated by reference in their entirety.

In certain embodiments, the targeting molecule is luteinizing hormone releasing hormone (LHRH) that targets LHRH receptor for use in treating breast cancer. See Leuschner et al., Breast Cancer Res Treat, 2006, 99:163-76, hereby incorporated by reference in its entirety.

In certain embodiments, the targeting molecule is CREKA peptide that targets clotted plasma proteins for use in treating breast cancer. See Simberg et al., Proc Natl Acad Sci USA, 2007, 104:932-6, hereby incorporated by reference in its entirety.

In certain embodiments, the targeting molecule is an antibody to prostate specific membrane antigen (PSMA) that targets PSMA for use in treating prostate cancer. See Serda et al., Mol Imaging, 2007, 6:277-88, hereby incorporated by reference in its entirety.

In certain embodiments, the disclosure contemplates targeting molecules in any of the disclosed embodiments that are antibodies or fragments or chimera, antibody mimetics, or aptamers or any molecular entity that selectively binds receptors, proteins, or glycoproteins that are more prevalent on cancer cells.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas in accordance with known methods. Hybridomas formed in this manner are then screened using standard methods, such as enzyme-linked immunosorbent assay (ELISA) and surface plasmon resonance analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

The modular structure of antibodies makes it possible to remove constant domains in order to reduce size and still retain antigen binding specificity. Engineered antibody fragments allow one to create antibody libraries. A single-chain antibody (scFv) is an antibody fragment where the variable domains of the heavy ($V_H$) and light chains ($V_L$) are combined with a flexible polypeptide linker. The scFv and Fab fragments are both monovalent binders but they can be engineered into multivalent binders to gain avidity effects. One exemplary method of making antibodies and fragments includes screening protein expression libraries, e.g., phage or ribosome display libraries. Phage display is described, for example, in U.S. Pat. No. 5,223,409.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. U.S. Pat. No. 7,064,244.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or back mutations. An antibody or fragment thereof may also be modified by specific deletion of human T cell epitopes or "deimmunization" by the methods disclosed in U.S. Pat. Nos. 7,125,689 and 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Antibody mimetics or engineered affinity proteins are polypeptide based targeting moieties that can specifically bind to targets but are not specifically derived from antibody $V_H$ and $V_L$ sequences. Typically, a protein motif is recognized to be conserved among a number of proteins. One can artificially create libraries of these polypeptides with amino acid diversity and screen them for binding to targets through phage, yeast, bacterial display systems, cell-free selections, and non-display systems. See Gronwall & Stahl, J Biotechnology, 2009, 140(3-4), 254-269, hereby incorporated by reference in its entirety. Antibody mimetics include affibody molecules, affilins, affitins, anticalins, avimers, darpins, fynomers, kunitz domain peptides, and monobodies.

Affibody molecules are based on a protein domain derived from staphylococcal protein A (SPA). SPA protein domain denoted Z consists of three α-helices forming a bundle structure and binds the Fc protion of human IgGI. A combinatorial library may be created by varying surface exposed residues involved in the native interaction with Fc. Affinity proteins can be isolated from the library by phage display selection technology. Affibody to HER-2 has been described. See Orlova et al., Cancer Res., 2007, 67:2178-2186, hereby incorporated by reference in its entirety.

Monobodies, sometimes referred to as adnectins, are antibody mimics based on the scaffold of the fibronectin type III domain (FN3). See Koide et al., Methods Mol. Biol. 2007, 352: 95-109, hereby incorporated by reference in its entirety. FN3 is a 10 kDa, 3-sheet domain, that resembles the $V_H$ domain of an antibody with three distinct CDR-like loops, but lack disulfide bonds. FN3 libraries with randomized loops have successfully generated binders via phage display (M13 gene 3, gene 8; T7), mRNA display, yeast display and yeast two-hybrid systems. See Bloom & Calabro, Drug Discovery Today, 2009, 14(19-20):949-955, hereby incorporated by reference in its entirety.

Anticalins, sometimes referred to as lipocalins, are a group of proteins characterized by a structurally conserved rigid β-barrel structure and four flexible loops. The variable loop structures form an entry to a ligand-binding cavity. Several libraries have been constructed based on natural human lipocalins, i.e., ApoD, NGAL, and Tlc. Anticalins have been generated for targeting the cytotoxic T-lymphocyte antigen-4 (CTLA-4) and the vascular endothelial growth factor (VEGF). See Skerra, FEBS J., 275 (2008), pp. 2677-2683, hereby incorporated by reference in its entirety.

The ankyrin repeat (AR) protein is composed repeat domains consisting of a 3-turn followed by two α-helices. Natural ankyrin repeat proteins normally consist of four to six repeats. The ankyrin repeats form a basis for darpins (designed ankyrin repeat protein) which is a scaffold comprised of repeats of an artificial consensus ankyrin repeat domain. Combinatorial libraries have been created by randomizing residues in one repeat domain. Different numbers of the generated repeat modules can be connected together and flanked on each side by a capping repeat. The darpin libraries are typically denoted NxC, where N stands for the N-terminal capping unit, C stands for the C-terminal capping domain and x for the number of library repeat domains, typically between two to four. A HER-2 binding darpin has been generated from a library containing two randomized repeat domains (N2C library) and by an affinity maturation strategy. Zahnd et al., J. Mol. Biol., 2007, 369:1015-1028, hereby incorporated by reference in its entirety.

Aptamers refer to affinity binding molecules identified from random proteins or nucleic acids libraries. Peptide aptamers have been selected from random loop libraries displayed on TrxA. See Borghouts et al., Expert Opin. Biol. Ther., 2005, 5:783-797, hereby incorporated by reference in its entirety. SELEX ("Systematic Evolution of Ligands by Exponential Enrichment") is a combinatorial chemistry technique for producing oligonucleotides of either single-stranded DNA or RNA that specifically bind to a target. Standard details on generating nucleic acid aptamers can be found in U.S. Pat. Nos. 5,475,096, and 5,270,163. The SELEX process provides a class of products which are referred to as nucleic acid ligands or aptamers, which has the property of binding specifically to a desired target compound or molecule. Each SELEX-identified nucleic acid ligand is a specific ligand of a given target compound or molecule. The SELEX process is based on the fact that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

Pharmaceutical Compositions

In certain embodiments, the disclosure relates to pharmaceutical compositions comprising particles disclosed herein and a pharmaceutically acceptable excipient. In certain embodiments, the composition is a pill or in a capsule or the composition is liquid solution such as an aqueous buffer, e.g., a pH of about 6.5, 7.0, or 7.5 or between 6 and 8. In certain embodiments, the pharmaceutically acceptable excipient is selected from a filler, glidant, binder, disintegrant, lubricant, and saccharide. Optionally, the pharmaceutical composition further comprises a second anticancer agent.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the particles in a certain part of the intestinal tract in a delayed manner. Examples of embedding compositions which can be used are polymeric substances and waxes.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to the particles, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Pharmaceutical compositions typically comprise an effective amount of particles and a suitable pharmaceutical acceptable carrier. The preparations can be prepared in a manner known per se, which usually involves mixing the particles according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the particles of the disclosure e.g., about 10, 25, 50, 100, 200, 300 or 400 mg per unit dosage.

The particles can be administered by a variety of routes including the oral, ocular, rectal, transdermal, subcutaneous, intravenous, intramuscular or intranasal routes, depending mainly on the specific preparation used. The particles will generally be administered in an "effective amount," by which it is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated.

Formulations containing particles described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, M D, 2000, and "Pharmaceutical dosage forms and drug delivery systems," 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard decomposition reactions which include, by way of example, oxidative reactions.

Examples

Protease-Linked Migrating IONPs with uPAR-Targeting Fragments ATF39 and ATF68

The amino terminal fragment (ATF, 135 aa) of uPA was used as a target ligand to develop uPAR-targeted theranostic IONPs. The yield and purity of recombinant ATF from bacterial cultures have been less than optimal due to the formation of undesirable aggregates. By removing of the hydrophobic amino acids that promote the formation of aggregates, uPAR targeting ligands (39 and 68 aa) with receptor-binding peptide regions were engineered as improvements. The ATF39 and ATF68 peptides can be produced in high yield (8.6 mg/L of bacterial culture, compared to 0.5 mg/L for 135 aa), increased purity and better solubility. Target specificity of the new ligand-conjugated IONPs was demonstrated in a human breast cancer PDX model derived from surgically resected and multidrug resistant breast cancer tissues obtained triple negative breast cancer patients.

The uPA-ATF with only the growth factor domain (ATF68) has improved physiological solubility and higher uPAR-targeting efficiency. In comparison with the full length ATF (135 aa), this short uPAR targeted ligand is an improved candidate to engineer the fusion targeting ligand ATF68-MMP14 with dual uPAR targeting and MMP14 protease activity.

$MMP14_{CD}$ IONP with uPAR-Targeting

Extensive tumor stroma in triple negative breast cancers creates a physical barrier for drug delivery. To address the challenge of delivery of the IONPs into cancer cells, fusion proteins of uPAR targeting ligands and catalytic domain of $MMP14_{CD}$ were developed to facilitate active targeting tumor and stromal and digesting of extracellular matrix proteins. The cDNA gene sequences of 39, 68 or 135 aa of human or mouse ATF were cloned at the 5'-end of the catalytic domain of the $MMP14_{CD}$ gene. ATF68-$MMP14_{CD}$ protein was produced in the bacterial expression system.

Human uPA-ATF68-$MMP14_{CD}$ protein sequence (SEQ ID NO: 4) underlined portion is the AFT68 segment, amino acids 2-69 (SEQ ID NO:2) and segment after, i.e., amino acids 71-246 including the double underlined zinc binding domain, is the $MMP14_{CD}$ (SEQ ID NO: 3).

(SEQ ID NO: 4)
MSNELHQVPSNCDCLNGGTCVSNKYFSNIHWCNCPKKFGGQHCEIDK

SKTCYEGNGHFYRGKASTDTMGAPIQGLKWQHNEITFCIQNYTPKVG

EYATYEAIRKAFRVWESATPLRFREVPYAYIREGHEKQADIMIFFAE

GFHGDSTPFDGEGGFLAHAYFPGPNIGGDTHFDSAEPWTVRNEDLNG

NDIFLVAVHELGHALGLEHSSDPSAIMAPFYQWMDTENFVLPDDDRR

GIQQLYGGESG

The protein was linked to IONPs comprising NIR-830 dye as reported in Satpathy et al., Small, 2014, 10(3):544-55, Xi et al J. Biophotonics 7, No. 6, 401-409 (2014), and Lee et al., ACS Nano, 2013, 7(3):2078-89. After labeled with near-infrared (NIR) dye on the thiol-group of Cysteine residues, $ATF_{MMP}$ with his-tag at C-termini was then conjugated to 10 nm core size IONP through two methods: 1) affinity binding to a surface polymer with NTA-Cu functional groups and 2) direct conjugation of amine groups of targeting peptides with carboxyl groups on the polymer surface via an amide bond. The polymer coated IONPs were obtained from Ocean Nanotech LLC, San Diego, CA. PEG-polymer coated IONP has a hydrodynamic size of about 12 nm, and then increases to be about 19 nm after conjugating with ATF is conjugated. ATF-MMP conjugated IONP has a hydrodynamic size of about 24 nm.

To determine if conjugation to nanoparticle affects its proteolysis activity, MMP14 activity of unconjugated ATF-MMP and ATF-MMP-IONP was measured using a fluorogenic MMP14 substrate. About 80% of the proteolysis activity of ATF-MMP remained after being conjugated to the nanoparticle. It is believed that delivery of $ATF_{MMP}$-IONP to interstitial binding to stromal cells leads to protease activity on extracellular matrix to break intensive collagen fibers, resulting tiny holes that are permeable for targeted IONPs to migrate through stroma to reach tumor cells and deliver drugs into cancer cells.

Due to the presence of species specificity in the binding of ATF to uPAR, a fusion protein was produced with mouse ATF68 and MMP14$_{CD}$. Such as mouse uPAR targeted ligand is very useful for the evaluation of the effect of targeting tumor endothelial and stromal cells as well as tumor cells on intratumoral nanoparticle delivery and distribution since all tumor stroma components originate from the mouse. Systemic delivery of NIR-830-mATF68-MMP14$_{CD}$-IONPs led to accumulation of the IONPs in the tumors in 4T1 mouse mammary tumor model. Moreover, stronger optical signals were detected in the tumors of the mice that received NIR-830-ATF68-MMP14$_{CD}$-IONPs than that of NIR-830-ATF68-IONPs or NIR-830-MMP14$_{CD}$, indicating that a higher level of the IONPs accumulate in the tumor.

Figure 5A:
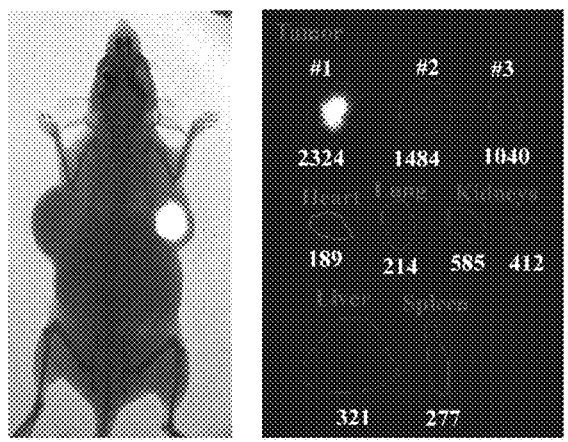
FIG. 5A shows data on evaluation of the efficiency of targeted delivery of nanoparticles by the combination of targeting to tumor cells and tumor stromal cells and MMP-14-mediated extracellular matrix degradation. A mixture of NIR-830 dye labeled human ATF68 and mouse ATF68 or human ATF68-MMP14$_{CD}$ and mouse ATF68-MMP14$_{CD}$ was used so that the nanoparticles could target to uPAR expressing human cancer cells and mouse-derived stromal cells. The tumor-bearing mice received 200 pmol of different IONPs every two days for two injections. Optical imaging was performed 48 hours following the last injection. A. Whole body non-invasive NIR optical imaging and ex vivo organ imaging in a primary human breast cancer model derived from a surgically resected and multi-drug resistant triple negative breast cancer tissue. Although ATF68- or MMP-14$_{CD}$ conjugated IONPs could target to tumors and produce optical signals, there were marked differences in the signal intensity among multiple tumor lesions in the same mouse. It is possible that inter-tumoral heterogenicity in the tumor stromal structure and cellular components affected nanoparticle delivery into tumors.
Figure 5B:
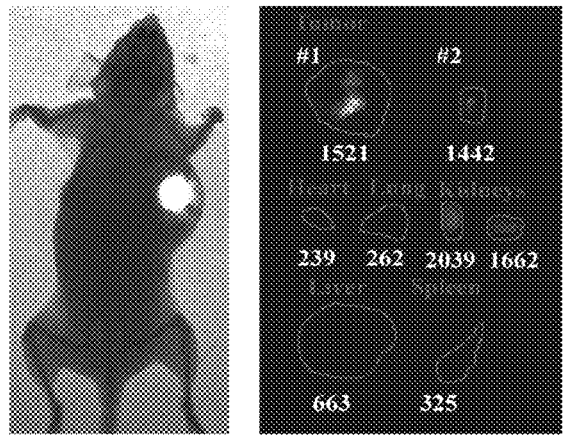
FIG. 5B shows results for NIR-830 dye MMP-14$_{CD}$ conjugated IONPs.
Figure 5C:
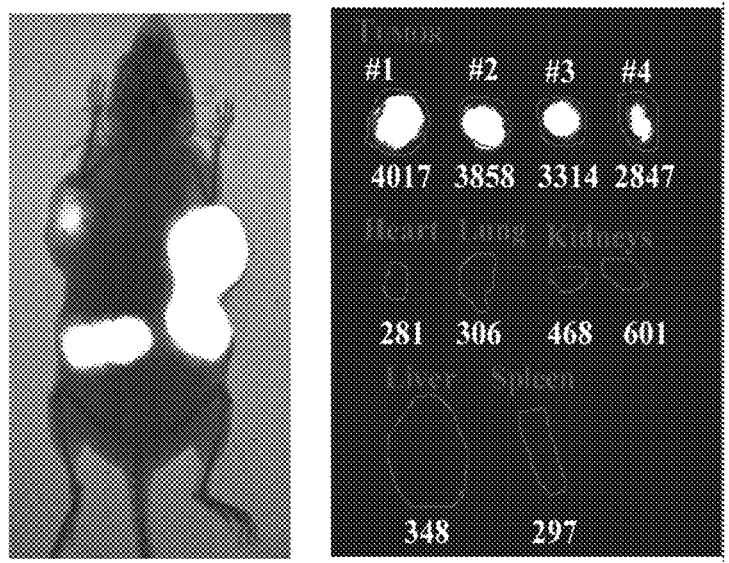
FIG. 5C shows results for the tumor-bearing mice that received NIR-830-ATF68-MMP-14$_{CD}$-IONPs. High levels of optical signals were detected in all four tumor xenograft in a mouse, suggesting that a targeting ligand with MMP14CD has the ability to enhance intratumoral nanoparticle delivery and distribution. In ex vivo images, the numbers showed the mean optical signals of tumors and normal organs. Lined areas were size and location of tumors and normal organs, which showed that in the tumors obtained from the mice that received ATF68- or MMP-14$_{CD}$ conjugated IONPs, there were tumor areas without strong optical signals. Tumors from the mice that received NIR-830-ATF68-MMP-14$_{CD}$-IONPs had strong signals in almost all tumor areas.
Figure 6:
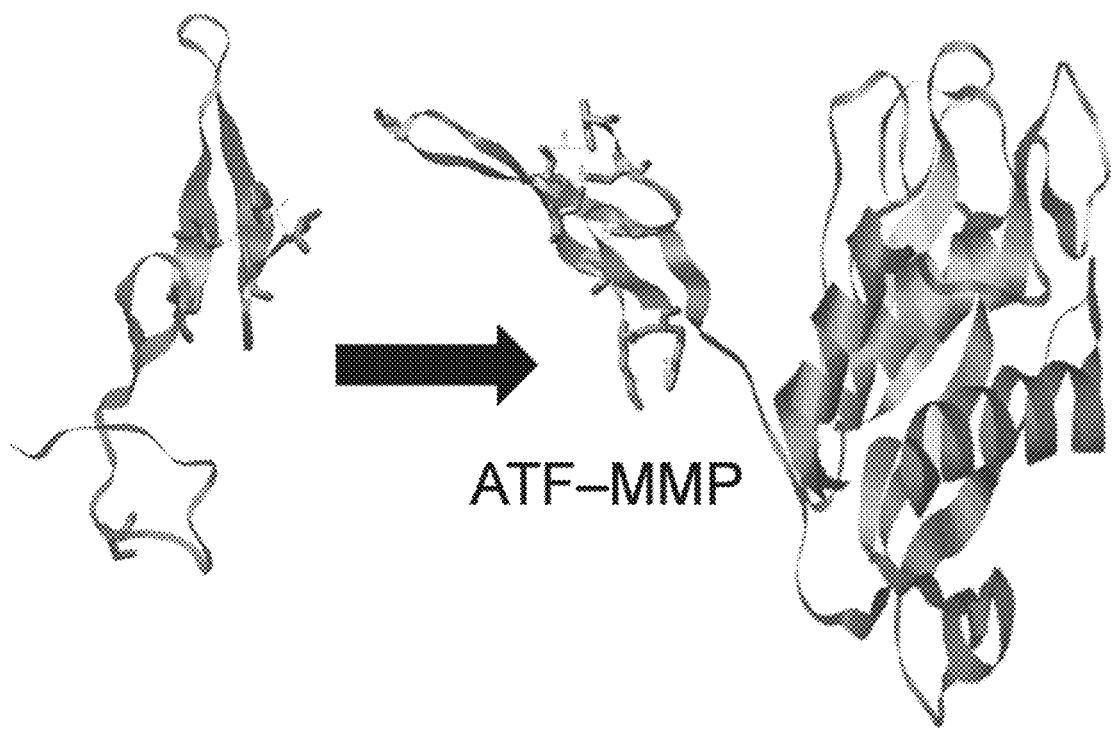
FIG. 6 illustrates the fusion of ATF68 and the MMP14$_{CD}$.
Figure 7A:
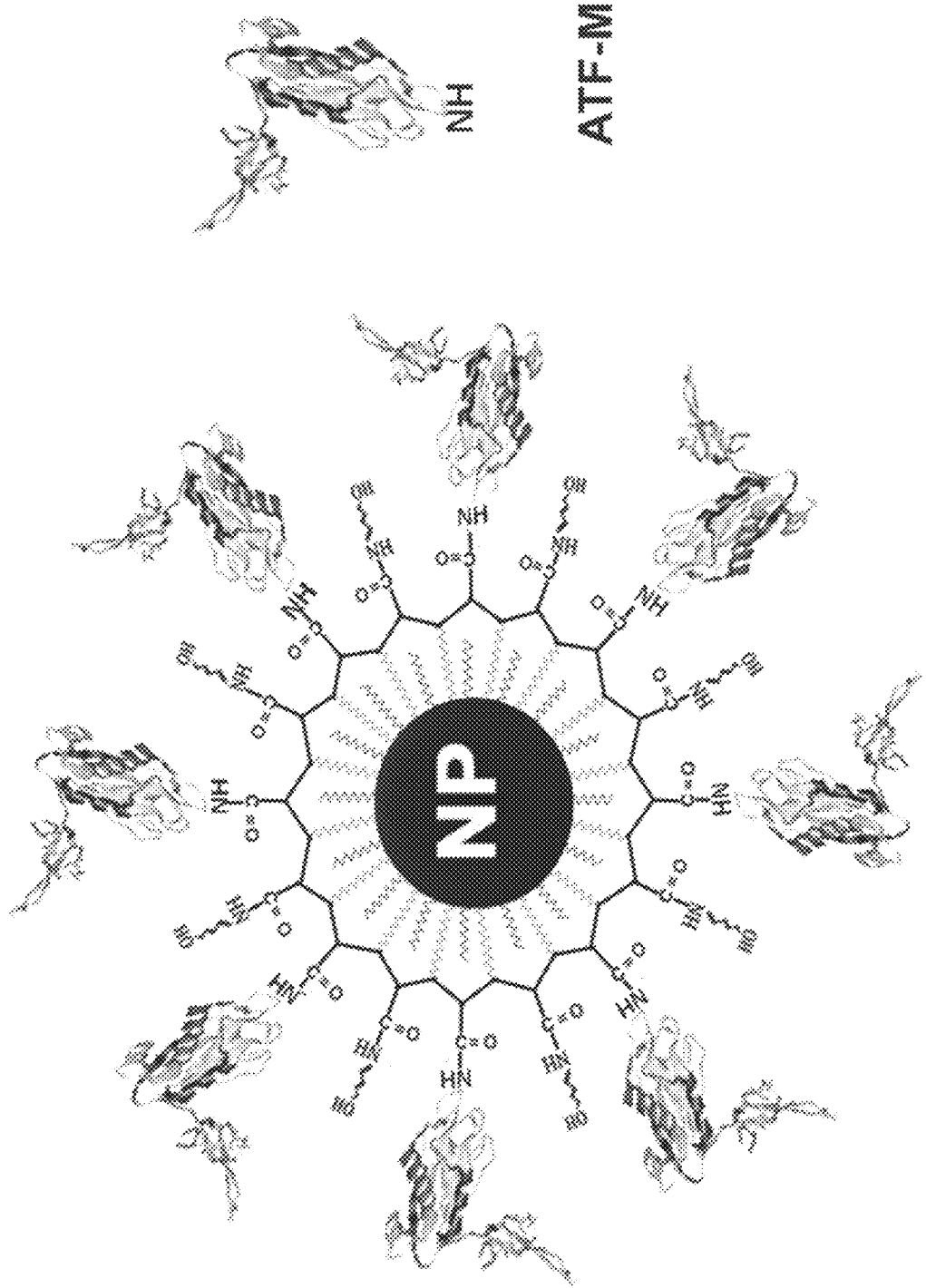
FIG. 7A illustrates ATF68-MMP14CD-IONPs
Figure 7B:
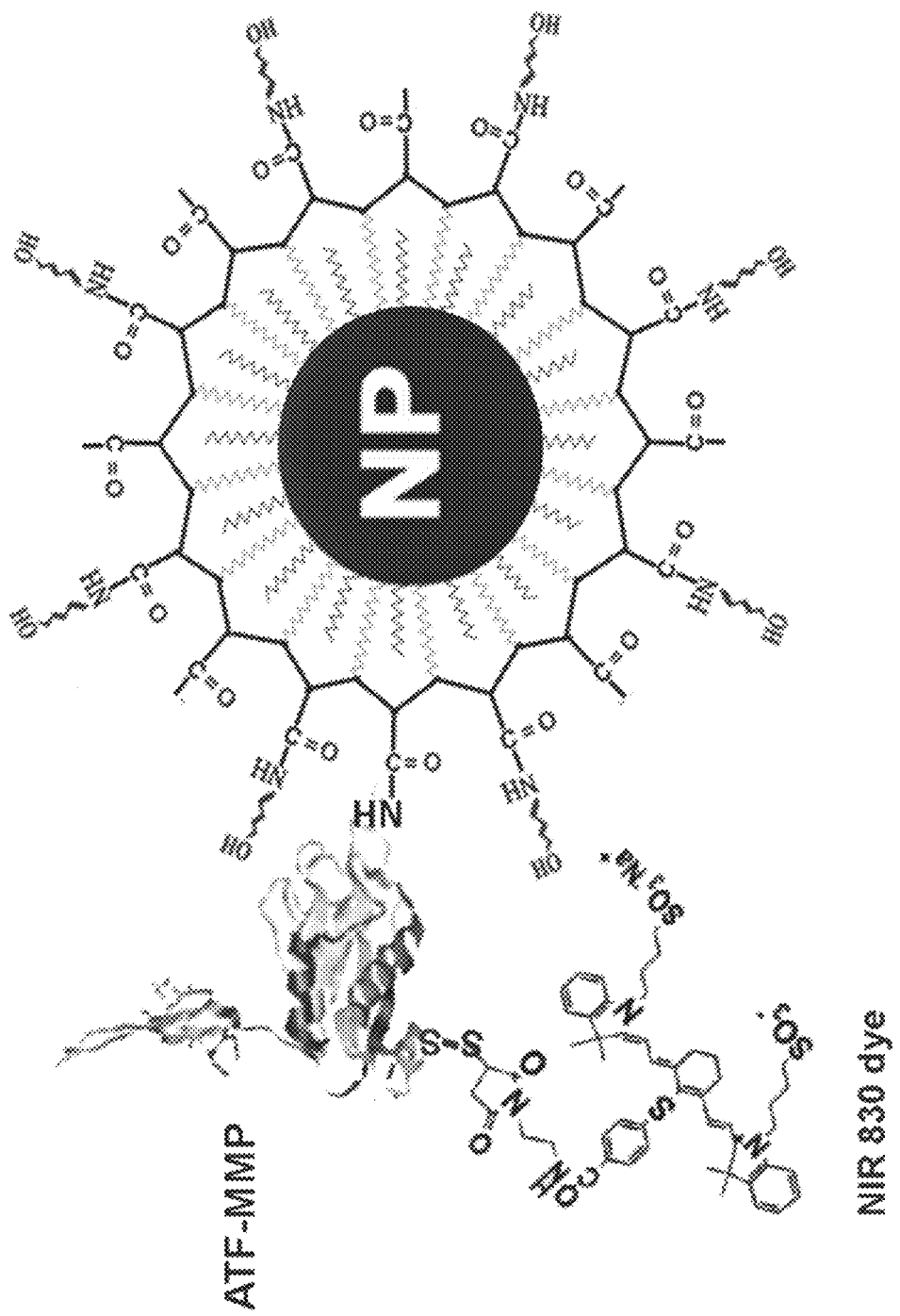
FIG. 7B illustrates NIR-830-ATF68-MMP14$_{CD}$-IONPs.

The effect of a significant increase on intratumoral delivery and improved intratumoral distribution of the nanoparticles was further confirmed in a human breast cancer patient-derived xenograft model. In this study, a mixture of human ATF68 and mouse ATF68 to conjugate the IONPs were used so that they can efficiently target to both human tumor cells and mouse derived tumor stromal cells. Following systemic delivery of 200 pmol of NIR-830-human +mouse ATF68-MMP14$_{CD}$-IONPs every 48 hours for two injections, non-invasive optical showed markedly higher level of the nanoparticle accumulation in the tumor of the mice that received NIR-830-hATF68-MMP14$_{CD}$-IONPs, compared with NIR-830-hATF68-IONPs with MMP14$_{CD}$, or NIR-830-MMP14$_{CD}$-IONPs. MMP14$_{CD}$ itself has the ability of targeted delivery of IONPs into tumors, most likely due to its membrane-binding property. However, histological examination of tumor tissue sections using Prussian blue staining showed that the level of accumulation in the tumors received hATF68-MMP14$_{CD}$-IONP was significantly higher than that of either NIR-830-hATF68-IONPs, or NIR-830-MMP14$_{CD}$-IONPs. Furthermore, much more ATF68$_{MMP}$14$_{CD}$ targeted IONPs were found in the tumor central areas, compared to hATF68-IONPs without MMP14$_{CD}$ or IONPs conjugated with MMP14$_{CD}$ alone (FIG. 5A-C).

The ATF$_{MMP}$ conjugated nanoparticle acts as an imaging probe and drug carrier. The nanoparticles are not limited to magnetic iron oxide nanoparticles. These targeted nanoparticles may be conjugated with other targeting ligands, e.g., ATF$_{MMP}$ and another cancer cell targeted ligand, such as IGF-1, Her2 affibody, and EGF or single chain antibody against EGFR, to improve targeting and intratumoral cell drug delivery in heterogeneous tumor cells.

In certain embodiments, the disclosure contemplates further conjugation with a near infrared dye, NIR-830, labeled ATF$_{MMP}$ as peptide targeted optical imaging probes for detection of uPAR receptor expression in tumors, or NIR-830-ATF68-MMP14 conjugated nanoparticle imaging probe for multimodal imaging.

In certain embodiments, simultaneous conjugation of separate targeting peptides and separate MMP catalytic domain directly onto a nanoparticle is also contemplated. However, it is more desirable to have both in the same polypeptide to save the conjugation sites on the surface of nanoparticles for adding therapeutic agents linked to the surface.

Figure 1B:
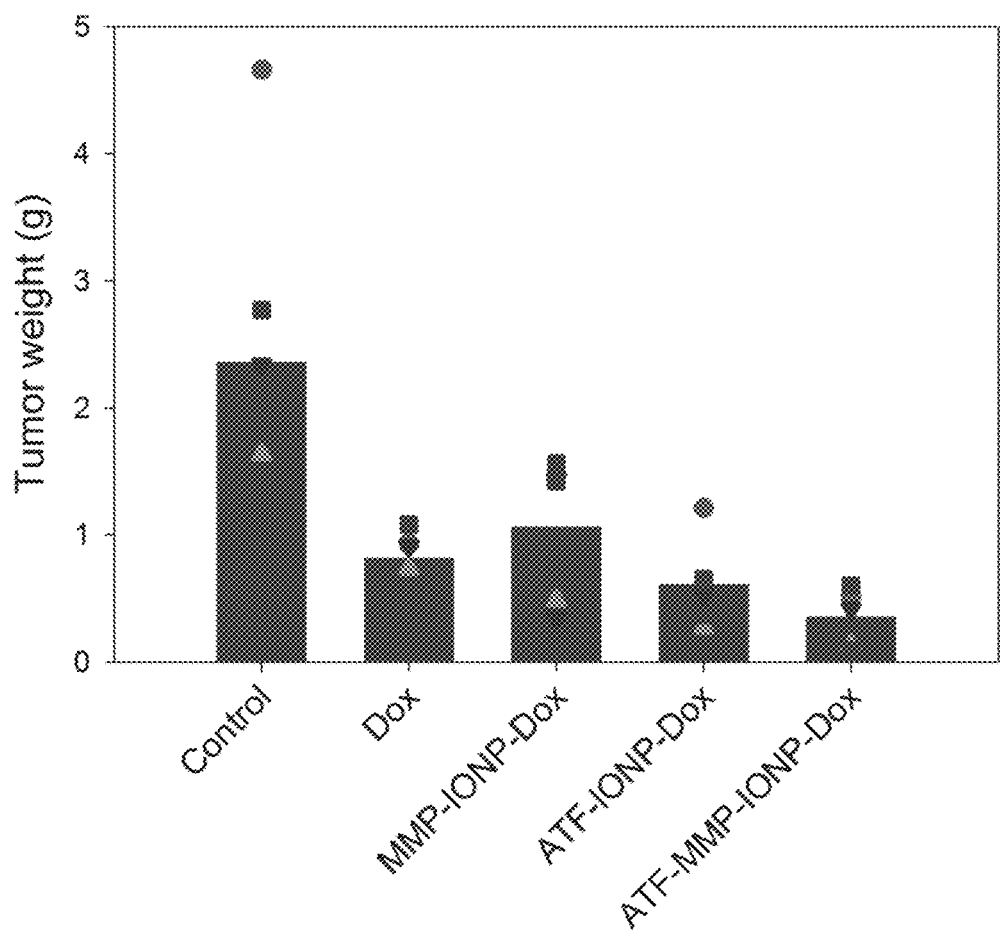
FIG. 1B shows data on for different treatments indicating tumor weights after the whole procedure of NP-treatment.
Figure 1C:
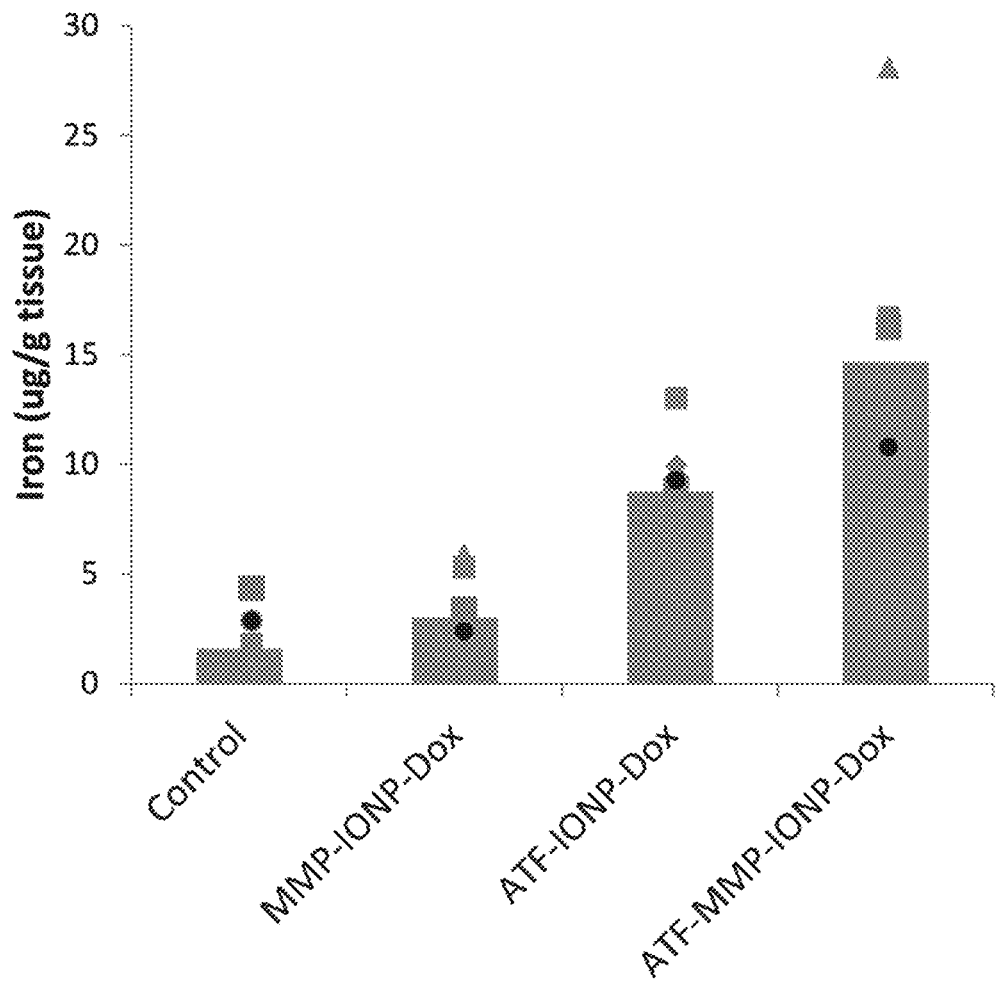
FIG. 1C shows data on iron accumulation in tumors after NP-treatment using chemical analysis of iron concentration in tumor tissue lysates.
Figure 2:
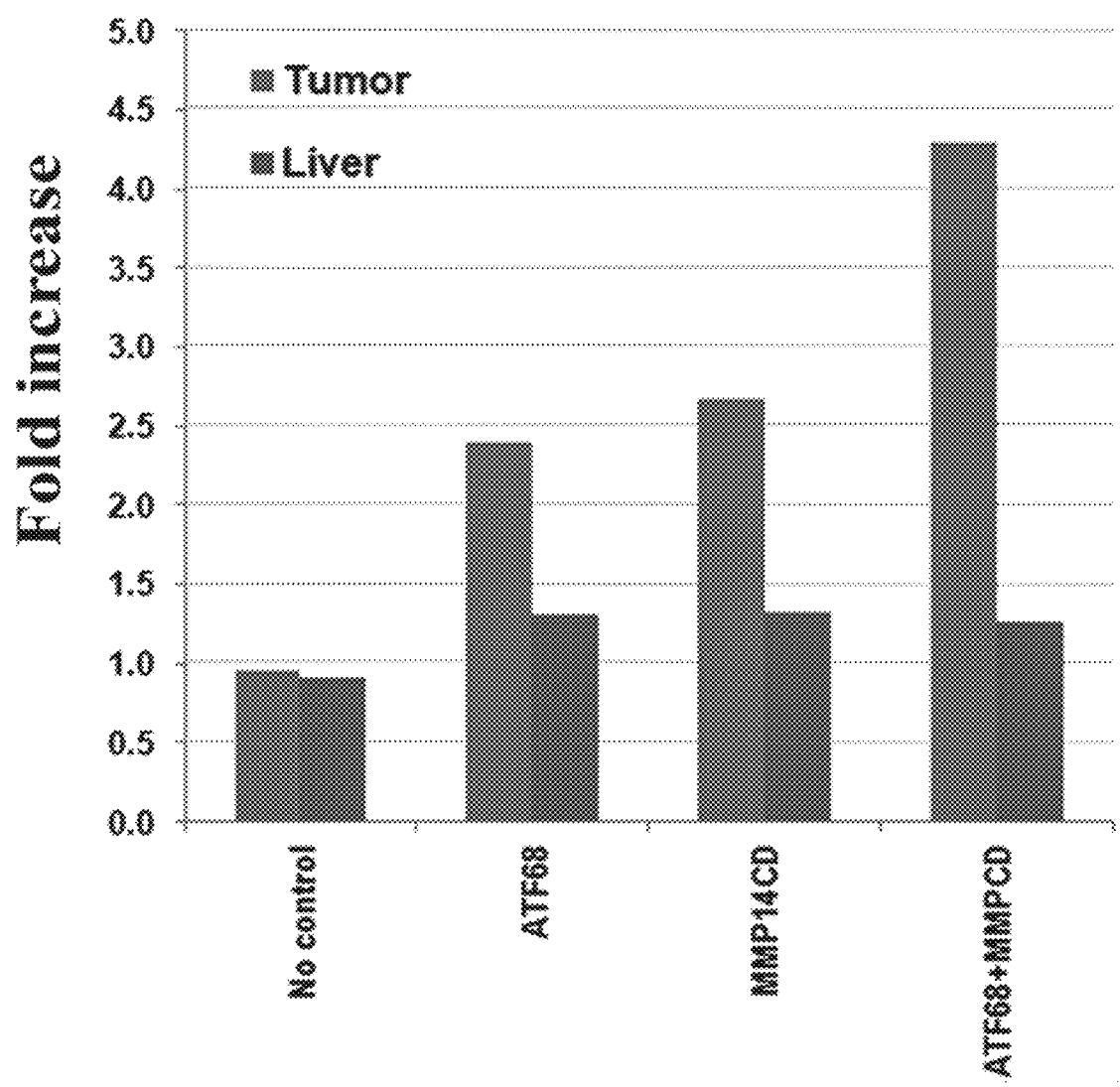
FIG. 2 shows data on MMP14 activity on $ATF_{MMP}$-IONPs indicating an improved targeted delivery in a human breast cancer patient derived xenograft (PDX) model. Tumor bearing mice received two i.v. injections of NIR-830-$ATF_{MMP}$-IONPs (400 picomol). Optical imaging was performed 48 hrs following the injection. Only one of the three tumors in the mouse received ATF-IONPs had strong optical signal. All four tumors in the mouse received $ATF_{MMP}$-IONP had very strong optical signals. An increase in IONP accumulation was found in $ATF_{MMP}$-IONP treated tumors, compared to ATF-IONP or MMP-IONP treated tumors.
Figure 3:
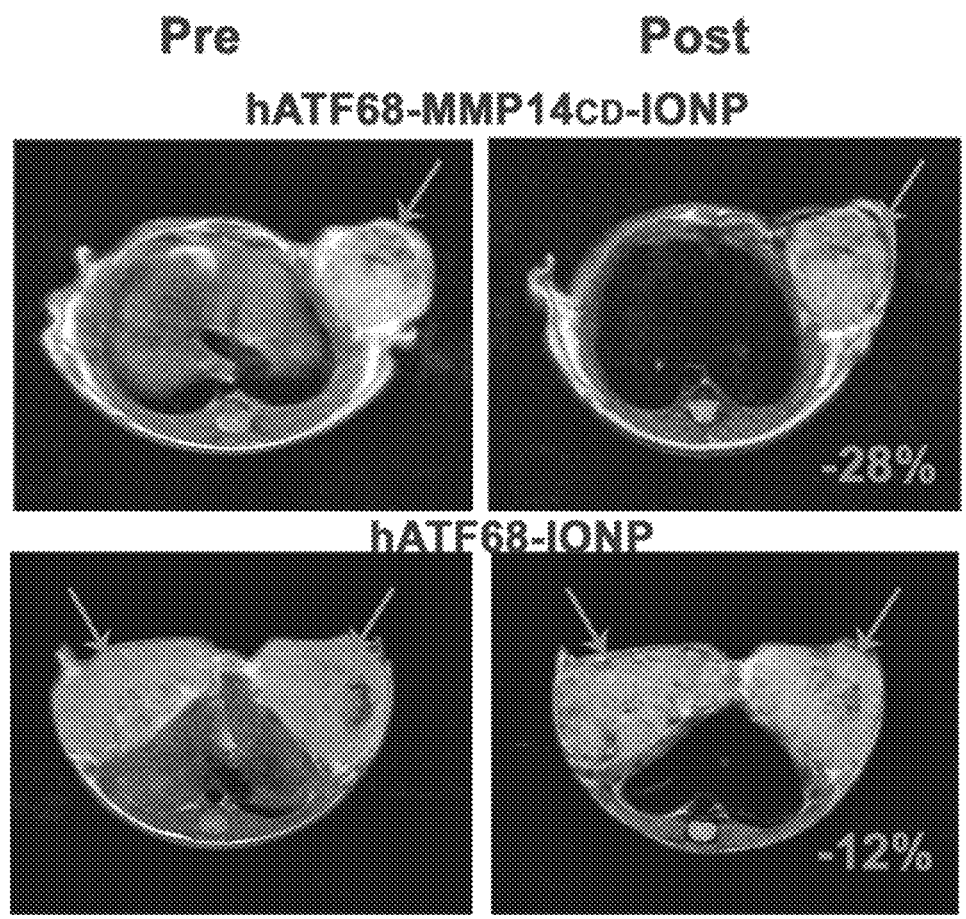
FIG. 3 shows T2-weighted MRI detection of IONP accumulation of different nanoparticles. Numbers are parentage of MRI signal decrease compared with pre-contrast images.
Figure 4:
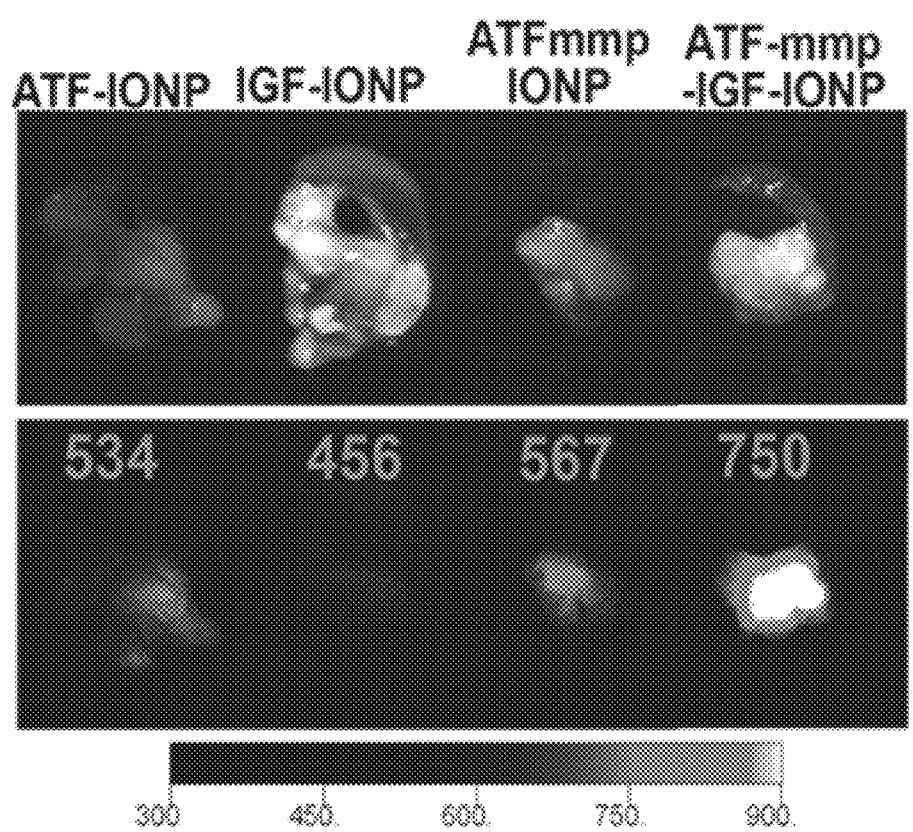
FIG. 4 shows data on a dual receptor targeted $ATF_{MMP}$-IGF-IONP indicating enhanced the intra-tumoral IONP delivery and distribution. Nude mice bearing human pancreatic PDX tumors received $ATF_{MMP}$-IGF-IONP, ATF-IONP, IGF-IONP, or $ATF_{MMP}$-IONP (400 picomol) via the tail vein for two injections. Ex vivo optical imaging also showed a high signal in the tumor treated with $ATF_{MMP}$-IGF-IONP. Dual receptor targeting showed significant MRI signal decrease (40% dual targeting with MMP) as compared from single targeting (~10 to 18%).

Enhanced Nanoparticle Drug Delivery LED to Increased Anti-Tumor Effects Following Systemic Delivery ATF$_{MMP}$-IONP Carrying Dox in an Orthotopic Human Breast PDX Cancer Model Doxorubicin, a commonly used chemotherapy drug, was encapsulated into IONPs as reported in Yang et al., J Biomed Nanotechnol. Dec. 1, 2008; 4(4): 439-449. Following systemic delivery of 5 mg/Kg Dox equivalent dose of various IONPs once week for six treatments, significant tumor growth inhibition was detected in ATF$_{MMP}$-IONP-Dox treated tumors compared with control, free Dox, nontargeted MMP-IONP-Dox and ATF-IONP-Dox treated groups (FIGS. 1A-1C). Although non-targeted MMP-IONP-Dox have been shown to be able to deliver into tumors via leaking tumor vessels and high collagen substrate in the tumor, mouse group treated with MMP-NP-Dox did not show any therapeutic effect and sometime, had increased tumor growth compared to the control no-treatment group. Therefore, ATF mediated targeting and internalization of nanoparticle-drug is important for effective cancer therapy. Increased IONP-drug delivery was determined by chemical analysis of iron concentration in tumor lysates. The highest iron content was also detected in ATF$_{MMP}$-IONP-Dox treated tumors compared to ATF-IONP treated tumors. Similar results were obtained from human breast cancer PDX models derived from two patients.

Multiplex Receptor Targeting Using ATF$_{MMP}$P and a Tumor Cell Surface Receptor Targeting Ligand Further Enhances Intratumoral Nanoparticle Delivery uPAR is expressed in invasive and aggressive tumor cells, and its expression on tumor cells is heterogeneous. To ensure effective receptor mediated internalization of nanoparticle drugs into all tumor cells, dual receptor targeted IONP were prepared by conjugating both NIR-830-dye labeled ATF$_{MMP}$ and insulin growth factor 1 (IGF-1) to IONP. Insulin growth factor receptor 1 is expressed uniformly in most tumor cells. It is also expressed at intermediate to high level in tumor stromal fibroblasts and macrophages. However, it is not expressed in tumor vessel endothelial cells. The combination of targeting both receptors should facilitate nanoparticle drugs across tumor vessels, penetrating through tumor stromal barriers, and efficiently delivering nanoparticle-drug into tumor cells. Supporting our hypothesis, Systemic administration of dual receptor targeted IONPs into mice bearing human pancreatic PDX tumors had a significantly higher level of IONPs in the tumors than that of tumors received single receptor targeted IGF-IONP, ATF-IONP, or ATF$_{MMP}$-IONP. MRI result showed 40% T2 signal decrease in the tumor of the mice that received dual targeted IONPs while the tumors of the mice that received single targeted IONPs had 14 to 22% T2 signal decrease. Ex vivo optical imaging of the excised pancreatic tumors further confirmed the increased nanoparticle delivery. Histological analysis using Prussian blue staining revealed a high level of IONPs in both orthotopic pancreatic cancer and liver metastasis. All three receptor targeted IONPs were found in tumor metastases in the liver, spleen and peritoneal cavity.

Conjugation of the ATF$_{MMP}$ targeting ligands to nanoparticles resulted in nanoparticle imaging probes and drug carriers with improved extravasation by targeting uPAR expressing tumor endothelial cells; improved binding to tumor stromal fibroblasts and macrophages that increases retention of the nanoparticles in tumor tissues; improved digestion of stromal matrix proteins enabling penetration of the nanoparticles through tumor stroma to reach tumor cells, and improved receptor-mediated internalization of nanoparticle-drug that promotes intratumoral drug delivery.

SEQUENCE LISTING

```
Sequence total quantity: 10
SEQ ID NO: 1                    moltype = AA   length = 4
FEATURE                         Location/Qualifiers
source                          1..4
                                mol_type = protein
                                organism = synthetic construct
SEQUENCE: 1
GFLG                                                                        4

SEQ ID NO: 2                    moltype = AA   length = 68
FEATURE                         Location/Qualifiers
source                          1..68
                                mol_type = protein
                                organism = synthetic construct
SEQUENCE: 2
SNELHQVPSN CDCLNGGTCV SNKYFSNIHW CNCPKKFGGQ HCEIDKSKTC YEGNGHFYRG           60
KASTDTMG                                                                    68

SEQ ID NO: 3                    moltype = AA   length = 11
FEATURE                         Location/Qualifiers
source                          1..11
                                mol_type = protein
                                organism = synthetic construct
SEQUENCE: 3
HELGHALGLE H                                                                11

SEQ ID NO: 4                    moltype = AA   length = 246
FEATURE                         Location/Qualifiers
source                          1..246
                                mol_type = protein
                                organism = synthetic construct
SEQUENCE: 4
MSNELHQVPS NCDCLNGGTC VSNKYFSNIH WCNCPKKFGG QHCEIDKSKT CYEGNGHFYR           60
GKASTDTMGA PIQGLKWQHN EITFCIQNYT PKVGEYATYE AIRKAFRVWE SATPLRFREV          120
PYAYIREGHE KQADIMIFFA EGFHGDSTPF DGEGGFLAHA YFPGPNIGGD THFDSAEPWT          180
VRNEDLNGND IFLVAVHELG HALGLEHSSD PSAIMAPFYQ WMDTENFVLP DDDRRGIQQL          240
YGGESG                                                                    246

SEQ ID NO: 5                    moltype = AA   length = 11
FEATURE                         Location/Qualifiers
source                          1..11
                                mol_type = protein
                                organism = synthetic construct
SEQUENCE: 5
HEXXHXXGXX H                                                                11

SEQ ID NO: 6                    moltype = DNA  length = 23
FEATURE                         Location/Qualifiers
source                          1..23
                                mol_type = other DNA
                                organism = synthetic construct
SEQUENCE: 6
gaggctggct tcatccactg ccc                                                   23

SEQ ID NO: 7                    moltype = AA   length = 6
FEATURE                         Location/Qualifiers
source                          1..6
                                mol_type = protein
                                organism = synthetic construct
SEQUENCE: 7
GGGGGG                                                                      6

SEQ ID NO: 8                    moltype = AA   length = 5
FEATURE                         Location/Qualifiers
source                          1..5
                                mol_type = protein
                                organism = synthetic construct
SEQUENCE: 8
GGGGT                                                                       5

SEQ ID NO: 9                    moltype = AA   length = 6
FEATURE                         Location/Qualifiers
source                          1..6
                                mol_type = protein
                                organism = synthetic construct
SEQUENCE: 9
GGGPPP                                                                      6
```

| | | |
|---|---|---|
| SEQ ID NO: 10 | moltype = AA  length = 7 | |
| FEATURE | Location/Qualifiers | |
| source | 1..7 | |
| | mol_type = protein | |
| | organism = synthetic construct | |
| SEQUENCE: 10 | | |
| GGGAPPP | | 7 |

What is claimed is:

1. A method of treating cancer comprising administering to a subject in need thereof an effective amount of a nanoparticle comprising an anticancer agent,
   wherein the nanoparticle is conjugated to a fusion polypeptide comprising a targeting polypeptide and a protease polypeptide having a catalytic domain,
   wherein the targeting polypeptide comprises the amino acid sequence of SEQ ID NO: 2,
   wherein the protease polypeptide having a catalytic domain comprises the amino acid sequence motif depicted in SEQ ID NO: 5.

2. The method of claim 1, wherein the protease polypeptide comprises SEQ ID NO: 3.

3. The method of claim 1, wherein the fusion polypeptide comprises SEQ ID NO: 4.

4. The method of claim 1, wherein the anticancer agent is doxorubicin.

5. The method of claim 1, wherein the anticancer agent is gemcitabine.

6. The method of claim 1, wherein the anticancer agent is cisplatin.

7. The method of claim 1, wherein the cancer is breast cancer.

8. The method of claim 1, wherein the cancer is triple negative breast cancer.

9. The method of claim 1, wherein the cancer is pancreatic cancer.

10. The method of claim 1, wherein the cancer is skin cancer.

11. The method of claim 1, wherein the cancer is head and neck cancer.

12. The method of claim 1, wherein the cancer is liver cancer.

13. The method of claim 1, wherein the cancer is sarcoma.

14. The method of claim 1, wherein the cancer is lung cancer.

15. The method of claim 1, wherein the cancer is prostate cancer.

* * * * *